(12) United States Patent
Korkala et al.

(10) Patent No.: US 12,029,541 B2
(45) Date of Patent: Jul. 9, 2024

(54) BIOIMPEDANCE MEASUREMENT CONFIGURATION

(71) Applicant: Polar Electro Oy, Kempele (FI)

(72) Inventors: Seppo Korkala, Kempele (FI); Tuomas Hartikainen, Oulu (FI); Juhani Kemppainen, Oulu (FI)

(73) Assignee: Polar Electro Oy, Kempele (FI)

( * ) Notice: Subject to any disclaimer, the term of this patent is extended or adjusted under 35 U.S.C. 154(b) by 841 days.

(21) Appl. No.: 16/665,363

(22) Filed: Oct. 28, 2019

(65) Prior Publication Data

US 2020/0060576 A1 Feb. 27, 2020

Related U.S. Application Data

(63) Continuation-in-part of application No. PCT/EP2019/065069, filed on Jun. 10, 2019.

(30) Foreign Application Priority Data

Jun. 11, 2018 (EP) .................................... 18176972

(51) Int. Cl.
*A61B 5/053* (2021.01)
*A61B 5/00* (2006.01)
(Continued)

(52) U.S. Cl.
CPC .......... *A61B 5/0535* (2013.01); *A61B 5/0205* (2013.01); *A61B 5/0245* (2013.01);
(Continued)

(58) Field of Classification Search
CPC ........... A61B 5/25; A61B 5/256; A61B 5/282; A61B 5/6804; A61B 5/6805; A61B 5/28; A61B 5/053; A61B 5/0205; A61B 5/683
See application file for complete search history.

(56) References Cited

U.S. PATENT DOCUMENTS 5,178,154 A * 1/1993 Ackmann ............ A61B 5/0535
600/526
7,725,187 B1 * 5/2010 Nabutovsky ......... A61B 5/7207
607/19
(Continued)

FOREIGN PATENT DOCUMENTS

CN 1370503 A 9/2002
JP 2015173768 A * 10/2015 ......... A61B 5/02416
(Continued)

OTHER PUBLICATIONS

International Search Report and Written Opinion received for PCT Application Serial No. PCT/EP2019/065069 dated Jul. 3, 2019, 13 pages.

(Continued)

*Primary Examiner* — Eun Hwa Kim
(74) *Attorney, Agent, or Firm* — FisherBroyles, LLP

(57) ABSTRACT

A garment is made of flexible material that includes a first measurement electrode integrated into the garment at a first location, a second measurement electrode integrated into the garment at a second location different from the first location, and a measurement circuitry configured to measure bioimpedance by using the first measurement electrode and the second electrode and to transmit the measured bioimpedance and to measure electrocardiogram by using at least one of the first measurement electrode and the second electrode or another electrode. The garment is an upper body garment, in which the first measurement electrode is disposed above a heart level and the second measurement electrode is disposed below the heart level.

15 Claims, 15 Drawing Sheets

(51) Int. Cl.
  *A61B 5/0205* (2006.01)
  *A61B 5/0245* (2006.01)
  *A61B 5/0535* (2021.01)
  *A61B 5/11* (2006.01)
  *A61B 5/25* (2021.01)

(52) U.S. Cl.
  CPC .............. *A61B 5/1118* (2013.01); *A61B 5/25* (2021.01); *A61B 5/6804* (2013.01); *A61B 5/6831* (2013.01); *A61B 5/742* (2013.01); *A61B 2562/0219* (2013.01)

(56) References Cited

U.S. PATENT DOCUMENTS

| | | | |
|---|---|---|---|
| 2005/0124901 A1 | 6/2005 | Misczynski et al. | |
| 2005/0192488 A1 | 9/2005 | Bryenton et al. | |
| 2008/0114220 A1* | 5/2008 | Banet ................... | A61B 5/021 600/382 |
| 2008/0287770 A1 | 11/2008 | Kurzweil et al. | |
| 2011/0092834 A1 | 4/2011 | Yazicioglu et al. | |
| 2011/0288605 A1* | 11/2011 | Kaib ................... | A61B 5/6823 607/5 |
| 2014/0288436 A1 | 9/2014 | Venkatraman et al. | |
| 2015/0366504 A1 | 12/2015 | Connor | |
| 2016/0143592 A1 | 5/2016 | Martikka et al. | |
| 2016/0302677 A1* | 10/2016 | He ....................... | A61B 5/1102 |

FOREIGN PATENT DOCUMENTS

| | | | | |
|---|---|---|---|---|
| WO | WO-9909884 A1 * | 3/1999 | ......... | A61B 5/02028 |
| WO | WO-0203861 A1 * | 1/2002 | ........... | A61B 5/0402 |
| WO | 2006/009627 A2 | 1/2006 | | |
| WO | WO-2011077097 A1 * | 6/2011 | ........... | A61B 5/0402 |
| WO | 2018/055228 A1 | 3/2018 | | |

OTHER PUBLICATIONS

Ulbrich et al., "The Impact Shirt: Textile Integrated and Portable Impedance Cardiography", Physiological Measurement, Institute of Physics Publishing, Bristol, GB, vol. 35, No. 6, May 20, 2014, pp. 1181-1196.

European Search Report received for European Patent Application Serial No. 18176972 dated Oct. 3, 2018, 3 pages.

Office Action received for Chinese Patent Application No. CN201980046134.8, dated Sep. 21, 2023, 21 pages (including English Translation).

* cited by examiner

BIOIMPEDANCE MEASUREMENT CONFIGURATION

CROSS-REFERENCE TO RELATED APPLICATIONS

This application is a bypass continuation-in-part of international application no. PCT/EP2019/065069 filed Jun. 10, 2019 which claims priority from European Patent Application No. 18176972.0, filed Jun. 11, 2018, which are incorporated by reference herein in their entireties.

BACKGROUND

Field

The present invention relates to a field of physiological or biometric measurements and, in particular, a measurement configuration for measuring bioimpedance from a human body.

Description of the Related Art

A typical configuration for measuring bioimpedance includes a set of measurement electrodes disposable to contact with skin, a measurement circuitry for measuring bioimpedance from one or more of the electrodes, and a processing circuitry for processing measurement data. There may also be provided a communication circuitry for communicating the processed measurement data in a wired or wireless manner.

SUMMARY

The present invention is defined by the subject matter of the independent claim.

Embodiments are defined in the dependent claims.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
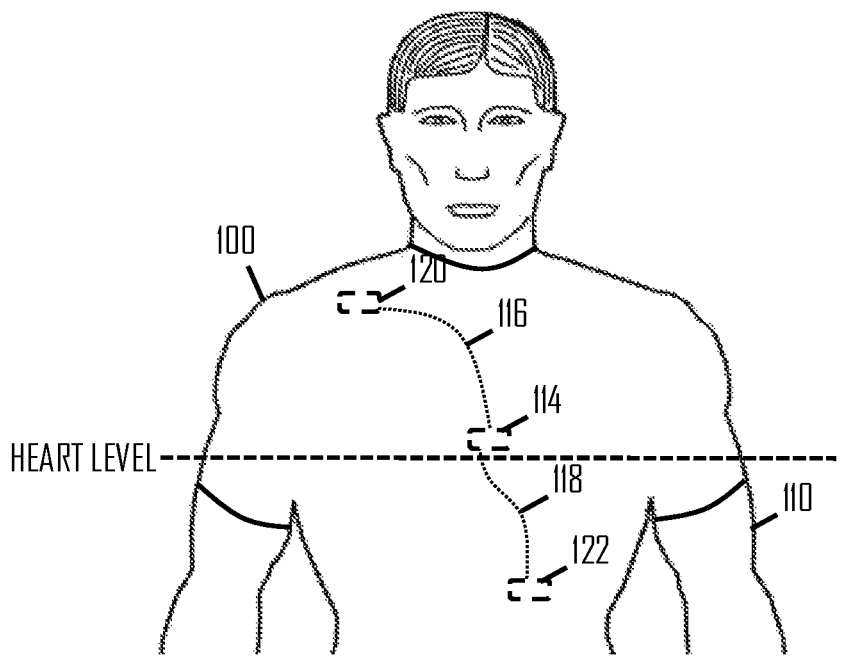
FIG. 1 illustrates a garment comprising a measurement circuitry according to an embodiment.

FIG. 1 illustrates an embodiment of a garment 100 made of flexible material. The garment comprises: a first measurement electrode 120 integrated into the garment at a first location, a second measurement electrode 122 integrated into the garment at a second location different from the first location, and a measurement circuitry 114 configured to measure bioimpedance by using the first measurement electrode and the second electrode and to transmit the measured bioimpedance, and to measure electrocardiogram (ECG) by using at least one of the first measurement electrode and the second electrode or another electrode, wherein the garment is an upper body garment, wherein the first measurement electrode is disposed above a heart level and the second measurement electrode is disposed below the heart level.

In another embodiment illustrated in FIGS. 22 and 23, the first measurement electrode and the second measurement electrode are disposed in the garment 100 such that, when the garment is worn in an intended manner, the first and second measurement electrodes are on the same side with respect to the heart level, e.g. above the heart level or below the heart level.

In an embodiment, the garment is a shirt, a vest, or a harness. The garment may equally be a bra or any other garment designed as an under layer to contact the skin of a human 110 (a user). The garment may be made of one or more of the following materials: nylon, polyamide, elastane, polyester, cotton, and wool.

In the embodiment of FIG. 1, the first measurement electrode 120 is disposed above the heart level, when the garment is worn by the user 110, while the second measurement electrode 122 is disposed below the heart level. The measurement circuitry 114 may be provided in a casing at an arbitrary location in the garment, and signal lines 116, 118 may connect the measurement electrodes 120, 122 to the measurement circuitry 114. The signal lines may be integrated into the garment.

Figure 2:
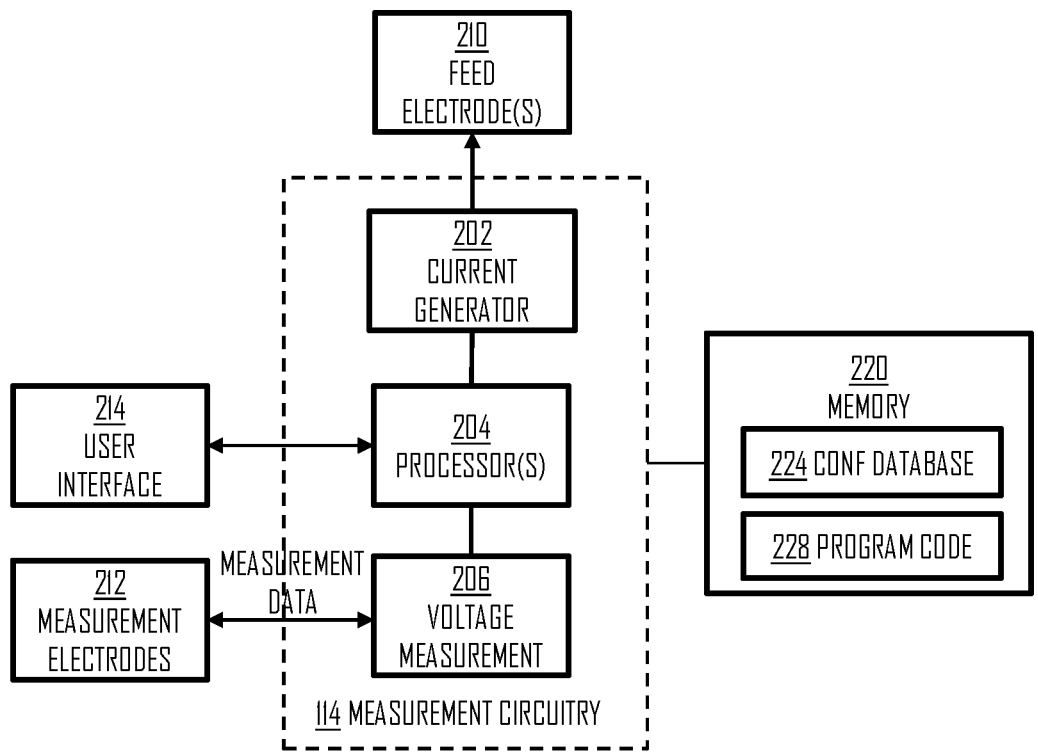
FIG. 2 an embodiment of the measurement circuitry.

Let us now describe the structure of the measurement circuitry 114 in greater detail with reference to FIG. 2 illustrating an embodiment of an apparatus. The apparatus may comprise at least one processor 204 and at least one memory 220 storing a computer program 228 comprising a program instructions that configure the at least one processor to execute the embodiments described herein. The apparatus may further comprise a user interface 214 comprising at least a display device and a user input device.

The bioimpedance measurement may be carried out by arranging signal feed electrodes 210 in the garment and, further arranging measurement the electrodes 212 in the garment. The measurement electrodes 212 may comprise the electrodes 120, 122. The measurement circuitry 114 may be configured to control the signal feed and the measurement, e.g. the following manner. One or more processors 204 may control a current generator 202 to output electric current to the feed electrodes 210. The current generator 202 may be signal synthesizer capable of outputting alternating current one various frequencies. The biompedance measurements may be used for estimating body composition, and multiple frequencies may be output for that purpose.

While the current generator is outputting current to the body, the processor 204 may configure a voltage measurement circuitry 206 to measure voltage between the measurement electrodes 212 and to acquire voltage measurement data from the measurement electrodes. The knowledge of the measured voltage U and the applied current I may then be used to compute the bioimpedance Z according to the well known formula: $Z=U/I$.

The measurement circuitry 114 may further comprise or have access to at least one memory 220. The memory 220 may store a computer program code comprising instructions readable and executable by the processor(s) 204 and configuring the above-described operation of the processor(s). The memory 220 may further store a configuration database 224 defining parameters for the processor(s), e.g. parameters for the current feed control.

The apparatus may further comprise a communication circuitry configured to transmit measurement data acquired by the measurement circuitry to an external device such as a smart phone or a wrist computer. The external device may be a training computer configured to monitor a physical exercise performed by the user. The communication circuitry may be a wireless communication circuitry supporting a wireless communication protocol such as ANT, ANT+, or Bluetooth®, e.g. Bluetooth Smart®.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), graphics processing units (GPUs), processors, controllers, micro-controllers, microprocessors, other electronic units designed to perform the functions described herein, or a combination thereof. For firmware or software, the implementation can be carried out through modules of at least one chipset (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

From the measured bioimpedance, other physiological characteristics such as a heart stroke volume may be computed. Patent publication US 2002/0193689 discloses one method of computing the stroke volume by using the bioimpedance and the ECG, and the processor 204 may employ such a method in some embodiments.

In the embodiment of FIG. 1, the electrodes 120, 122 may be used as both feed electrodes through which the electric current is applied and as voltage measurement electrodes. A switching mechanism may be applied which switches the function of the electrodes 120, 122 between the current feed and the voltage measurement. The switching mechanism may perform time-multiplexing and connect the electrodes either to the current generator 202 or the voltage measurement circuitry, under the control of the processor 204 and depending on the desired function of the electrodes 120, 122.

In a further embodiment, one or more of the electrodes 120 and 122 are further configured to measure the ECG. In such a case, the switching mechanism may further control switching of the electrodes to a differential amplifier used as a front-end in the ECG measurements.

Figure 3:
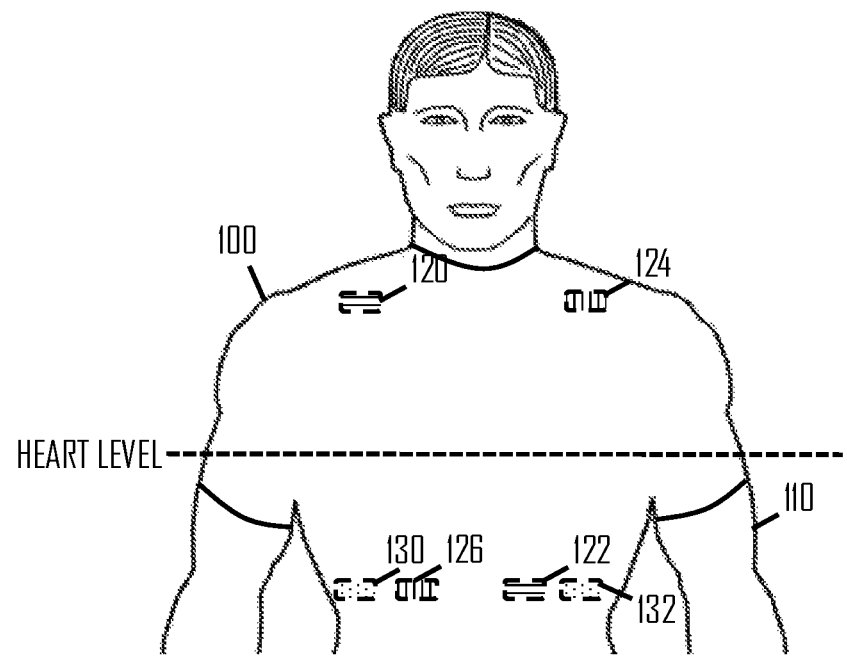
FIGS. 3 and 4 illustrate further embodiments of placement of the electrodes in the garment.
Figure 4:
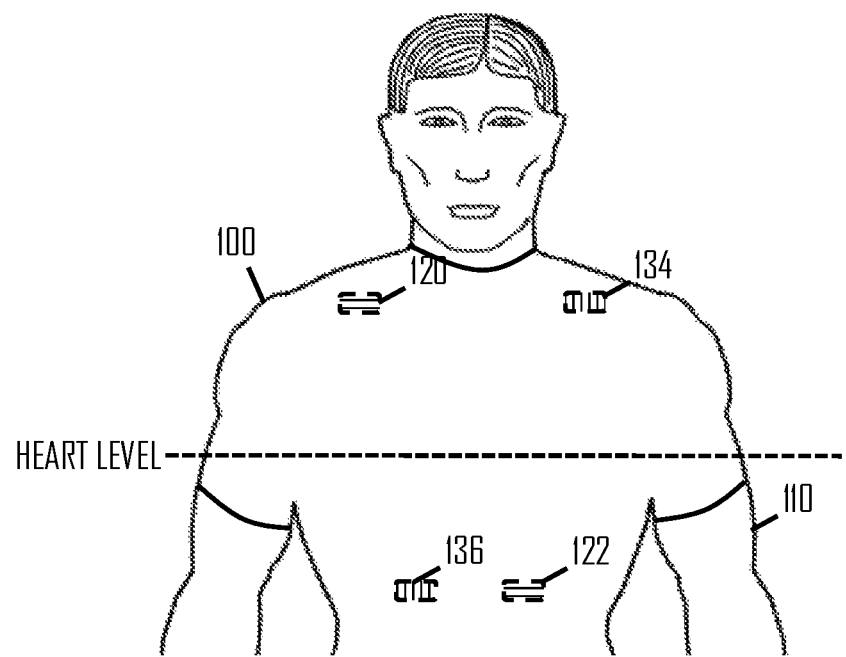

FIGS. 3 and 4 illustrate further measurement configurations according to other embodiments. In the embodiment of FIG. 3, there are further electrodes 124, 126, 130, 132. In the configuration, electrodes 120 and 122 may be used as the current feed electrodes and the electrodes 124 and 126 may be the measurement electrodes. As illustrated in FIG. 3, each electrodes is provided at a different location. The locations of the electrodes 120 to 126 may be selected such that a line drawn from the measurement electrode 124 to the measurement electrode 126 intersects with a line drawn from the feed electrode 120 to the feed electrode 122. This provides symmetricity between the current feed and the voltage measurement. The electrodes 130 and 132 may be configured as ECG measurement electrodes and disposed at an arbitrary location in the garment.

FIG. 4 illustrates an embodiment where the electrodes 124, 126, 130, 132 are replaced by electrodes 134 and 136 that are configured to function as both the voltage measurement electrodes for the bioimpedance measurements and as the ECG measurement electrodes by using the switching mechanism. In this embodiment as well, the feed electrodes and the measurement electrodes are disposed such that the above-mentioned lines will intersect.

In the embodiments of FIGS. 3 and 4, one of the feed electrodes is above the heart level while the other one of the feed electrodes is below the heart level. In a similar manner, one of the measurement electrodes is above the heart level while the other one of the measurement electrodes is below the heart level.

The garment may have a backside arranged to face a backside of the user and further have a front side arranged to face a front side of the user. In any one of the embodiments of FIGS. 1, 3, and 4, the electrode(s) 120, 124, 134 disposed above the heart level may be disposed at a neck or shoulder area of the garment on at least the backside of the garment. This improves the skin contact during a physical exercise such as running. In an embodiment, the electrode(s) above the heart level is/are elongated and extend(s) from the backside of the garment to the front side of the garment over a shoulder of the user. During the exercise, the shoulder area of the garment typically has the best skin contact, and this embodiment further improves the skin contact.

The electrode(s) 122, 126, 136 disposed below the heart level may be disposed in a chest area of the garment, wherein the garment is arranged to be form-fitting at the location of the second electrode. The form-fitting may be realized by the elastic material of the garment or by a strap in the garment.

In embodiments modified from those described above in connection with FIGS. 3 and 4, at least some of the electrodes may be disposed on an opposite side of the human body. For example, one or more or even all the electrodes 122, 126, 130, 132, 136 may be disposed on the back side of the body. Those electrodes disposed below the heart level may be disposed on the back side of the garment or on either side. In an embodiment, the garment comprises one or more electrodes disposed below the heart level on the back side and further electrode(s) disposed below the heart level on the front side.

In an embodiment, the feed electrodes may have a different shape than the measurement electrodes. For example, the measurement electrodes may be elongated while the feed electrodes may have a round or point shape. The point shape enables more accurate determination of the current path between the feed electrodes and, thus, simplifies the system configuration. Elongated measurement electrodes provide a better skin contact for the measurements and, thus, improved measurement accuracy.

Figure 5:
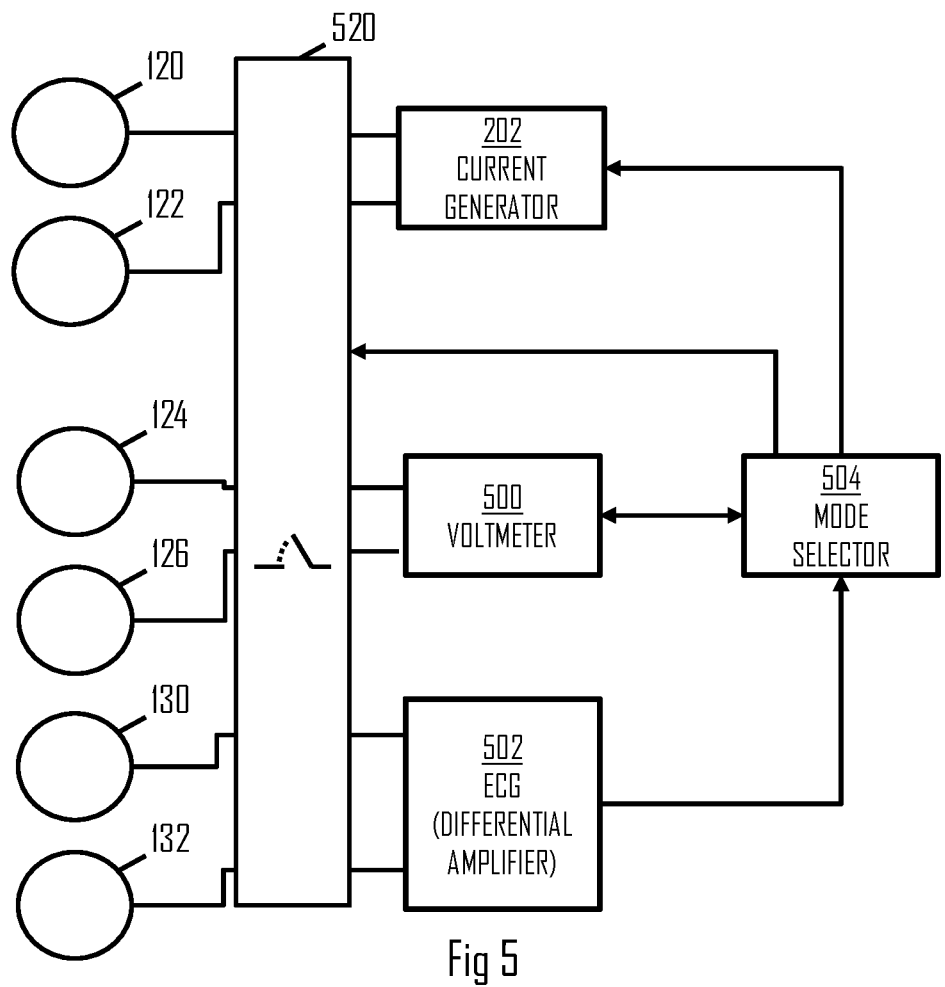
FIG. 5 illustrates an embodiment of an arrangement for switching a mode of one or more electrodes of the garment.

FIG. 5 illustrates a block diagram of the measurement circuitry comprising the switching mechanism 520. The switching mechanism 520 may be realized by one or more switches that perform(s) switching a function of at least one of the measurement electrodes between the ECG measurement and bioimpedance measurement. The switching mechanism 520 may comprise one or more electronic switches.

In an embodiment the switching mechanism 520 switches the function of the measurement electrodes between at least two of the following measurement modes: full ECG mode where all measurement electrodes are used to measure ECG, a full bioimpedance measurement mode where all measurement electrodes are used to measure bioimpedance, and a hybrid measurement mode where a first subset of the measurement electrodes are used to measure ECG and a second subset of the measurement electrodes are used to measure bioimpedance. The switching mechanism may be controlled by the processor 204. The processor 204 may comprise a mode selector circuitry 504 configured to perform a process for selecting a measurement arrangement according to the flow diagram of FIG. 6.

Figure 6:
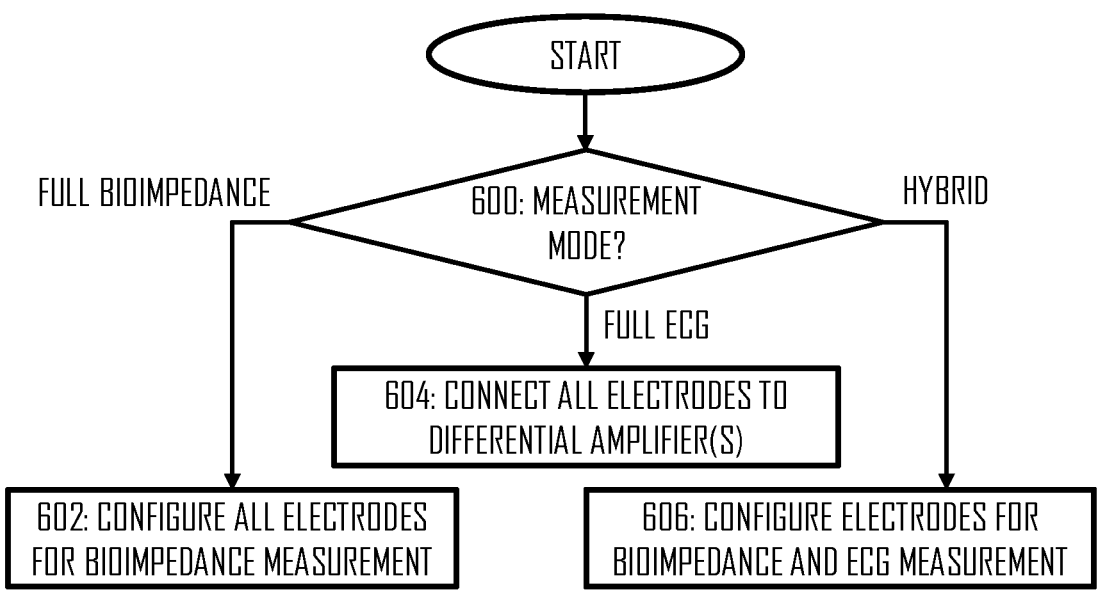
FIG. 6 illustrates a flow diagram of a process for configuring the operation of the electrodes of the garment according to an embodiment of the invention.

Referring to FIG. 6, the mode selector circuitry 504 selects the measurement mode in block 600. The selection may be made based on a measurement profile acquired on the basis of a user input, for example. Upon selecting the full ECG mode in block 600, the process may proceed to block 604 where the mode selector configures the switching mechanism 520 to couple all the electrodes 120 to 132 to inputs of an ECG measurement circuitry 502. The ECG measurement circuitry 502 may comprise a plurality of differential amplifiers, and each pair of electrodes 120 to 132 may be connected to inputs of one of the differential amplifier. For example, the switching mechanism 520 may couple the electrodes 120 and 122 to different inputs of one of the differential amplifiers, the electrodes 124 and 126 to different inputs of another one of the differential amplifiers, and the electrodes 130 and 132 to different inputs of yet another one of the differential amplifiers. In this manner, the switching mechanism may realize a multi-channel ECG measurement arrangement where two or more pairs of electrodes are connected to the ECG measurement circuitry 502. The mode selector 504 may further activate the ECG measurement circuitry 502 to start the multi-channel ECG measurements. The ECG measurement circuitry 502 may combine the ECG measurement signals received through the different measurement channels. Full ECG mode may be used when only the heart rate or heart activity is monitored, e.g. during a physical exercise.

Upon selecting the full bioimpedance mode in block 600, the process may proceed to block 602 where the mode selector 504 configures the switching mechanism 520 to couple all the electrodes 120 to 132 for bioimpedance measurements. In the full biompedance mode, the switching mechanism 520 may couple at least one pair of the electrodes for current feed and at least one pair of electrodes for voltage measurement. In an embodiment, the current feed electrodes may be coupled to a current generator 202 configured to feed constant current. In an embodiment, the voltage measurement electrodes are coupled to a voltmeter 500 configured to measure voltage between the voltage measurement electrodes while the current generator feeds the current.

In the embodiment using four electrodes, e.g. electrodes 120 to 126, electrodes 120 and 122 may be coupled to the current generator 202 for current feed and electrodes 124, 126 to the voltmeter 500, as described above in connection with FIG. 3. In the embodiment using six electrodes, e.g. electrodes 120 to 132, a measurement channels may be realized by coupling one or more of the electrodes 130, 132 also to the voltmeter 500. For example, a further voltage measurement may be realized between electrodes 124 and 132 and/or 124 and 130.

In the embodiment using only two electrodes, the switching mechanism may be configured to alternately switch the electrodes to the current generator 202 and to the voltmeter 500 with a determined frequency. In this manner, only two electrodes may be used when measuring the bioimpedance. The voltmeter may be configured to measure a voltage sample while the electrodes are coupled to the voltmeter and not take samples while the electrodes are coupled to the current generator.

The full bioimpedance mode may be used when measuring body composition, for example. In the full bioimpedance mode, the current generator may be configured to output currency one at least two frequencies, either simultaneously or in a time-multiplexed manner.

Upon selecting the hybrid mode in block 600, the process may proceed to block 606 where the mode selector 504 configures the switching mechanism 520 to couple a subset of the electrodes for the bioimpedance measurements and another subset of electrodes for the ECG measurements. This mode may be employed when measuring the stroke volume and heart rate during a physical exercise or when measuring the body composition and the heart rate simultaneously, for example.

In the hybrid mode, the switching mechanism may couple at least two electrodes to the ECG measurement circuitry 502, at least two electrodes to the current generator 202, and at least two electrodes to the voltmeter 500. In the embodiment of FIG. 3 using six electrodes, each electrode may be configured to a specific function in a fixed manner in the hybrid mode. For example, the electrodes 120, 122 may be coupled to the current generator 202, electrodes 124, 126 to the voltmeter 500, and electrodes 130, 132 to the ECG measurement circuitry 502.

In the embodiment using a reduced set of electrodes, e.g. four electrodes as in FIG. 4, the switching mechanism 520 may be configured to alternately switch the electrodes to the ECG measurement circuitry 502 and to the voltmeter 500 with a determined frequency. The voltmeter may be configured to measure a voltage sample while the electrodes are coupled to the voltmeter and not take samples while the electrodes are coupled to the ECG measurement circuitry. The ECG measurement circuitry 502 may be configured to measure an ECG sample while the electrodes are coupled to the ECG measurement circuitry and not take samples while the electrodes are coupled to the voltmeter.

In the embodiments using the alternating switching, the switching frequency may be higher than 60 Hertz (Hz).

Figure 7:
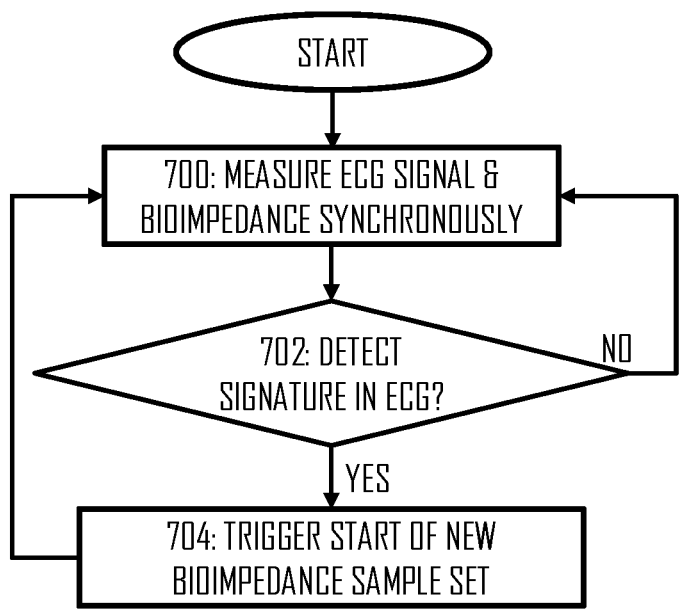
FIGS. 7 and 8 illustrate an embodiment for synchronising bioimpedance measurements with a cardiac cycle.

When computing the stroke volume from the bioimpedance, the ECG measurement signal may be used for acquiring a time reference for the stroke volume measurement. FIG. 7 illustrates an embodiment for acquiring a bioimpedance sample set for the stroke volume estimation by the processor(s) 204. Referring to FIG. 7, the process comprises measuring the ECG signal and the bioimpedance in a synchronous manner (block 700). The processor may maintain a time reference common to both measurements. When performing the switching between the ECG and voltage measurements, the switching frequency may be sufficiently high such that satisfactory synchronization accuracy is maintained.

Figure 8:
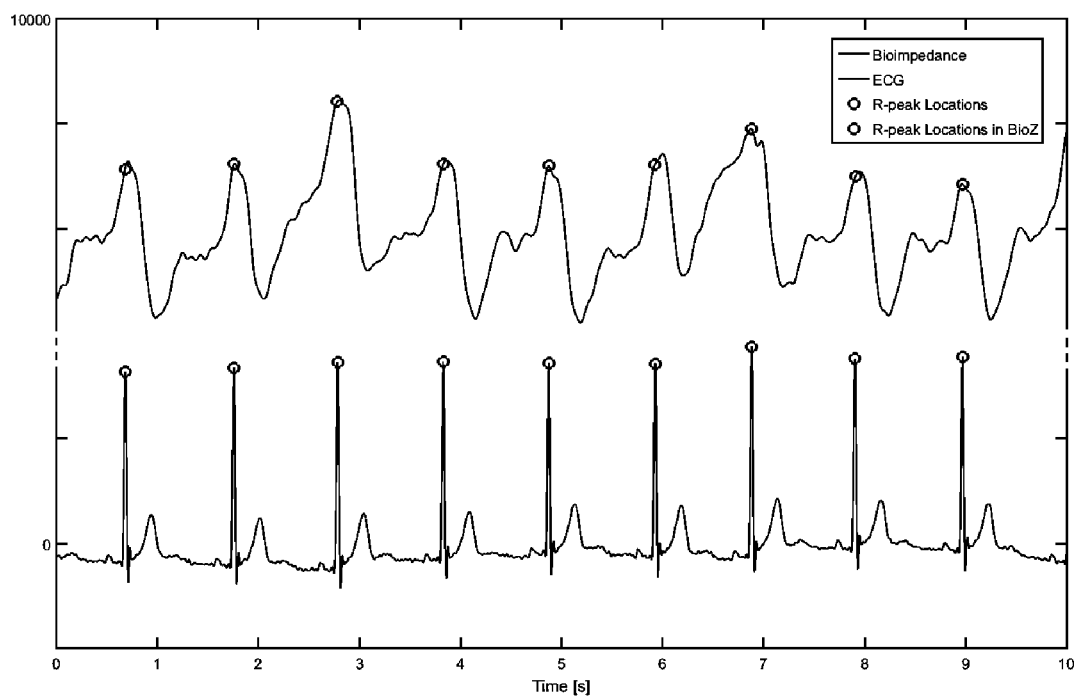

The processor may monitor for a signature in the ECG signal. R peak is a typical strong signature point which may be monitored. FIG. 8 illustrates a bioimpedance signal and, below that, an ECG signal. The R peaks are circled in the ECG signal. Upon detecting the signature in the ECG signal in block 702, the processor may trigger a start of a new bioimpedance sample set in block 704 (circles in the bioimpedance signal in FIG. 8). In this manner, the process of FIG. 7 may generate multiple sets of bioimpedance samples, e.g. for the stroke volume measurement. The process of FIG. 7 also synchronizes the stroke volume estimation with the cardiac cycle of the user.

In an embodiment, the processor performs averaging over the bioimpedance sample sets. The averaging may be smoothing where the samples having the same index in the respective sample set are averaged. Referring to FIG. 8 illustrating multiple sample sets of the bioimpedance samples, the averaging will result in an average bioimpedance sample set computed from the multiple sample sets of the bioimpedance samples. As FIG. 8 illustrates, the bioimpedance may be volatile, and the smoothing may improve the accuracy of the stroke volume estimation.

In an embodiment, the processor may further estimate respiratory rate from the signature. The respiratory rate may be computed from a phase of the ECG signal, for example. In another embodiment, the respiratory rate is computed by measuring R-R intervals of the ECG signal. The respiratory rate may be detected from the R-R intervals by using the knowledge that the R-R interval is shorter when the user inhales than when the user exhales. By monitoring this periodicity in the R-R intervals, the respiratory rate may be computed. The processor may compute the respiratory rate by using the measured bioimpedance instead of, or in addition to, the ECG. In an embodiment, the processor(s) 204 may perform motion compensation for the bioimpedance measurements. The garment may comprise one or more motion sensors integrated therein. In an embodiment, the motion sensors are integrated at a locations of the measurement electrodes, e.g. electrodes configured to measure the voltage, for example. In another embodiment, the motion sensor(s) is/are comprised in the same casing as the measurement circuitry.

Figure 9:
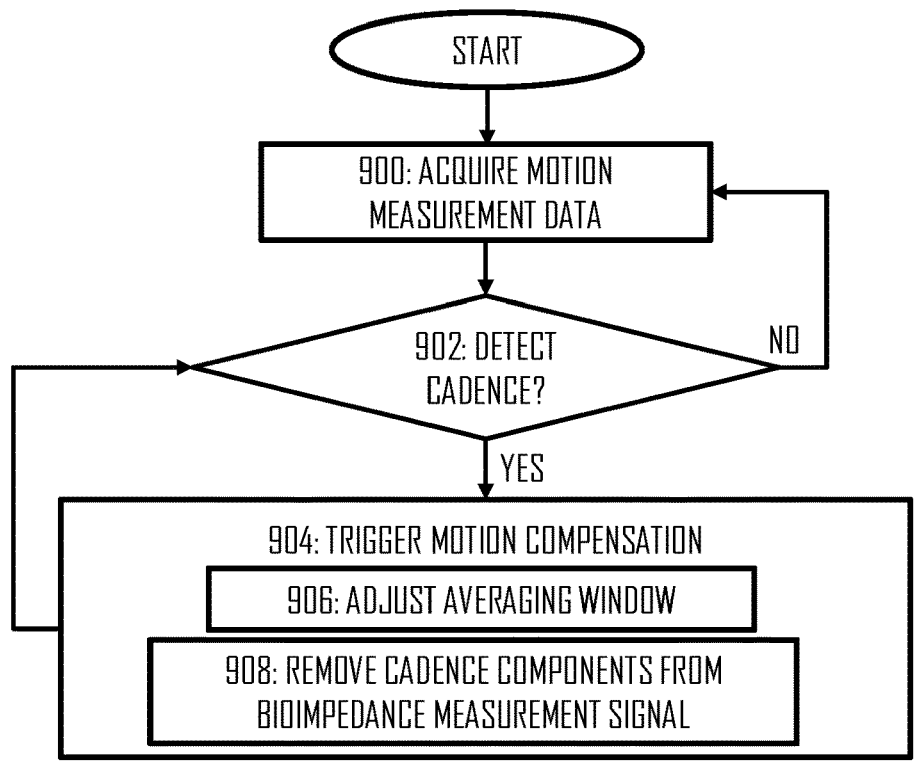
FIG. 9 illustrates a flow diagram of a process for performing motion compensation for a bioimpedance measurement signal according to an embodiment of the invention.

The motion sensor(s) may be configured to measure motion of the garment at the location(s) of the measurement electrodes, and the measurement circuitry may be configured to perform motion compensation for the measured bioimpedance on the basis of the measured motion. FIG. 9 illustrates an embodiment for performing the motion compensation by the measurement circuitry 114.

Referring to FIG. 9, the processor(s) may acquire motion measurement data from the motion sensor(s) in block 900. The processor may be configured to attempt detection of a cadence in the motion measurement data. Upon detecting the cadence in block 902, the processor may trigger a motion compensation algorithm to start motion compensation.

In an embodiment, the cadence is detected by computing a Fourier transform of the motion measurement data and performing peak detection for the transformed data. If a frequency component above a determine threshold has been detected, the processor may determine that cadence has been detected in block 902.

In an embodiment, the motion compensation in block 904 comprises adjustment of averaging window used in the above-described smoothing (block 906). The length of the averaging window, i.e. the number of sample sets to be included in the smoothing, may be determined on the basis of the cadence, for example. For a higher cadence, a larger window may be selected. Instead of cadence, another criterion may be used, e.g. training intensity acquired from a measured heart rate. For a higher intensity, a larger window may be selected. In another embodiment, the size of the window is also or alternatively dependent on an estimate of a signal-to-noise ratio of the bioimpedance measurement signal.

In an embodiment, the motion compensation in block 904 comprises an interference rejection algorithm (block 908). The interference rejection may attempt to detect a signal component having a frequency of the determined cadence and to remove the signal component from the bioimpedance measurement signal.

In yet another embodiment, the motion compensation may include using auxiliary data. For example, when performing stroke volume measurements and detecting cadence, poor signal-to-noise ratio, or another indicator for a need of motion compensation, the processor may use auxiliary data in the stroke volume estimation. For example, the processor may store a mapping table mapping a training intensities or heart rates to stroke volumes. Upon detecting the need for motion compensation, the processor may compute the stroke volume at least partially on the basis of the mapping table. In an embodiment, upon detecting cadence above a determined threshold or a signal quality below another determined threshold, the processor may use only the mapping table for the stroke volume estimation.

Let us now describe some embodiments regarding implementation of the electrodes and electronics in the garment.

In an embodiment, the material of the electrodes is thermoplastic polyurethane (TPU). Properties of TPU include elasticity, transparency, and resistance to oil, grease and abrasion which make them suitable for use in garments. Another option for the electrode material is silver.

Figure 10:
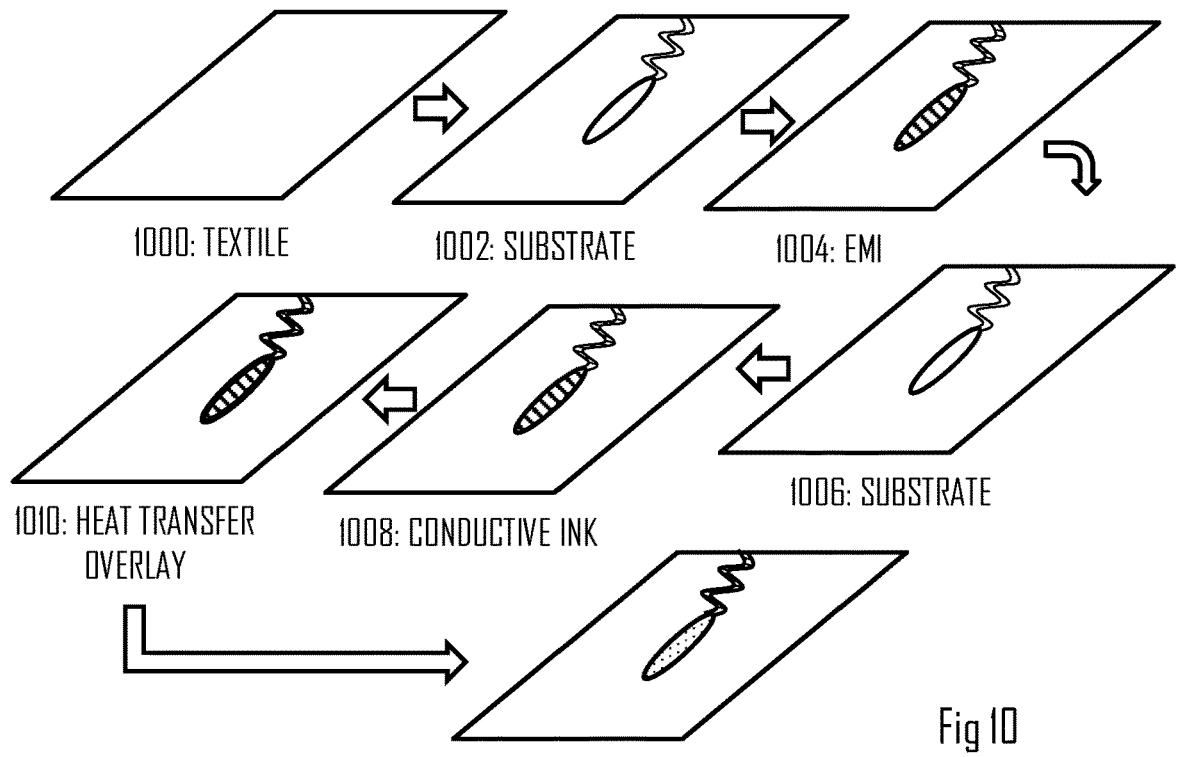
FIG. 10 illustrates stages and intermediate products of a manufacturing process for producing electrodes according to an embodiment of the invention.

In an embodiment, the electrodes are manufactured into the garment through a laminating or a printing process. Through printing, the electrodes may be arranged to form an arbitrary pattern in the garment. FIG. 10 illustrates the process in terms of intermediate products of the electrode during the process. First, a textile layer 1000 is provided wherein the textile layer is the garment or a part of the garment. A heat transfer substrate 1002 is then formed on the textile at an intended location of the electrode and the signal line connecting the electrode to the measurement circuitry. Thereafter, an EMI shield 1004 may be disposed on the substrate The EMI shield may be realized by a conductive ink printed on the substrate. The EMI shield 1004 may cover the intended locations of the electrode and the signal line, thus protecting them both. Then, a further substrate layer 1006 may be formed on the EMI shield to isolate the EMI shield from the electrode and the signal line. On the further substrate layer 1006, conductive ink 1008 may be disposed to form the signal lines and the electric connection between the signal line and the electrode. Thereafter, a heat transfer coverlay 1010 may be disposed on edges of the electrode location and, further, on the signal line to cover the signal line. This layer isolates the signal line and the conductive ink from the user's skin. Thereafter, the heat transfer coverlay may be covered with a heat transfer film comprising one or more through holes to enable electric coupling to the conductive ink 1008. On top of the heat transfer film, the electrode layer 1012 is formed from conductive thermoplastic, for example. The hole(s) in the heat transfer film at the location of the electrode enable the electric coupling between the electrode layer and the conductive ink 1008.

Figure 11:
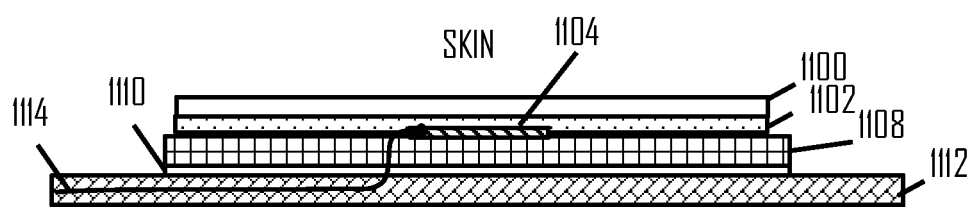
FIGS. 11 and 12 illustrate embodiments of a layered structure of an electrode in the garment.

In an embodiment, the electrodes are arranged to have a layered structure. FIG. 11 illustrates such an embodiment. In the embodiment of FIG. 11, a first layer 1100 arranged to contact the skin is a conductive layer made of the TPU, for example. This may form the electrode layer. The next layer may comprise the heat transfer film with the hole(s) and the coverlay 1102 isolating the first layer 1100 from the exterior, e.g. the garment's textile, and yet providing the electric coupling for the electrode layer. The layer 1102 may comprise the one or more holes for the electric coupling between the electrode and the signal line. The signal line is illustrates by numeral 1114 in FIG. 11. The first layer 1100 may contact a contact point 1104 such as a contact plate through the hole(s) in the layer 1102, and the signal line (e.g. 116 or 118) may be brought to the contact point 1104. Another TPU layer 1108 may be disposed on the heat transfer overlay layer. The TPU layer 1108 may be isolated from the contact point by an isolation member 1106. Then, a heat transfer film 1110 or the substrate layer 1002 may be provided as a coupling member to the garment 1112. The heat transfer film may act as glue and penetrate the textile material of the garment, thus fixing the other layers to the garment.

Figure 12:
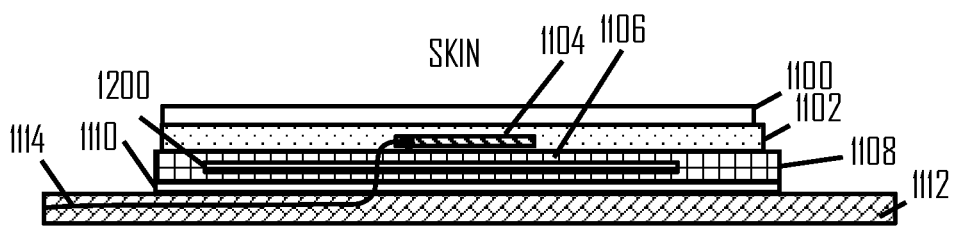

In another embodiment illustrated in FIG. 12, an electromagnetic interference (EMI) shield layer 1200 (1004 in FIG. 10) may be provided inside the TPU layer 1108 or between the TPU layer 1108 and the heat transfer coverlay 1102, for example. The EMI shield layer may be isolated from the contact point 1104, as in the embodiment of FIG. 10.

The signal line 116 or 118 may be sewn in the textile or provided on top of the textile. The signal lines may be formed of a conductive yarn. In an embodiment, EMI shielding is provided for the signal lines 116, 118 of the apparatus. The EMI shielding according to these embodiments may be suitable for any signal lines that conduct electric signals and are susceptible to the EMI. The signal line may comprise an electric conductor that may be formed by an electrically conductive thread or threading in an article of clothing, an apparel or a garment. The electric conductor may be isolated by an isolation layer protecting the electric conductor and isolating the electric conductor. On top of the electric conductor, the EMI shielding may be provided by arranging a conductive threading to cover the electric conductor. The conductive threading may be arranged on top of the electric conductor by stitching or sewing the conductive threading with a sewing machine. The conductive threading may be formed by using zigzag stitching such that the zigzag pattern covers the signal line without penetrating the isolation layer. The conductive threading may be sewn through a substrate in which the signal line is provided, e.g. a textile or a garment. When used in an application where the substrate is in contact with the user's skin, the conductive threading thus engages the user's skin and operates as a skin electrode for grounding the EMI.

In another embodiment, the shielding may be realized by using a coaxial yarn which is basically a yarn having a structure of a coaxial cable. An inner signal line may be surrounded by an isolation layer and a grounding protective layer. The coaxial signal line may be so thin that it can be sewn. The coaxial signal line may comprise two signal lines: one connected to the contact point 1104 and the other to the ground, e.g. the EMI shield 1200. In this manner, shielding for the signal line may be realized.

In yet another embodiment where two or more signal lines are drawn from one location to another, e.g. in the embodiment where the motion sensor is employed at the location of the electrode where the signal lines are drawn from the electrode to the location of the measurement circuitry, the signal lines may be twisted with respect to each other. Accordingly, a twisted pair signal line is formed which provides protection against EMI.

In an embodiment, the signal lines may be covered by a silicone or another protective material.

In an embodiment, the EMI shielding of the signal lines may be provided a conductive paste coating the signal lines.

Figure 13:
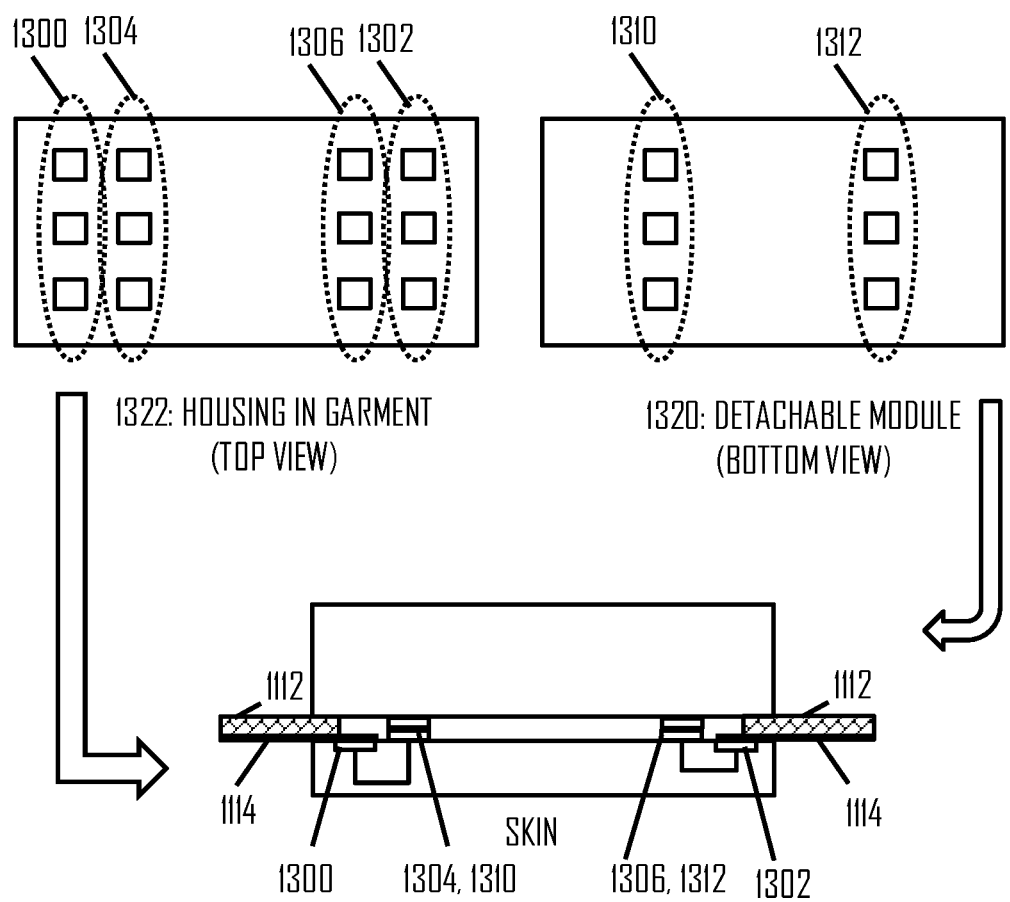
FIGS. 13 and 14 illustrate embodiments of a detachable electronics module for the garment.

In an embodiment, a casing housing the electronics including the measurement circuitry 114 is detachable from the garment. The casing may be waterproof and attached mechanically to the garment by using snap fastening, for example. The snap fastening may also align the casing with respect to the garment such that the signal lines in the garment will couple with the corresponding interfaces in the casing. FIG. 13 illustrates an example of such an embodiment.

Referring to FIG. 13, the measurement circuitry may comprise a housing 1322 integrated or attached to the garment 1112, e.g. in a fixed or permanent manner. The housing may function as a positioning member for the casing 1320 housing the measurement circuitry. The housing 1322 may comprise a first set of signal connectors 1300, 1302 that connect to the electrodes in the garment, e.g. the ECG electrodes and bioimpedance electrodes. The housing 1322 may comprise a second set of signal connectors 1304, 1306 configured to provide connection with respect connectors in the casing 1320. The connectors 1304, 1306 may be exposed when the module 1320 is detached from the housing 1322. The connectors 1300, 1302 may be covered, e.g. in the housing, and connecting in the housing to the respective signal lines 1114 leading to the respective electrodes. Internal wiring may be disposed in the housing 1322 to connect the connectors of the first set 1300, 1302 to the appropriate connectors of the second set 1304, 1306, as illustrated in the bottom of FIG. 13.

The casing 1320 may comprise the set of connectors 1310, 1312 that are disposed such that the connectors connect to the appropriate connectors of the second set 1304, 1306 when the casing 1320 is attached to the housing. Internal wiring may be provided in the module to connect the connectors to respective components of the measurement circuitry, e.g. to the differential amplifier 502, voltmeter 500, and/or the current generator 202.

Figure 14:
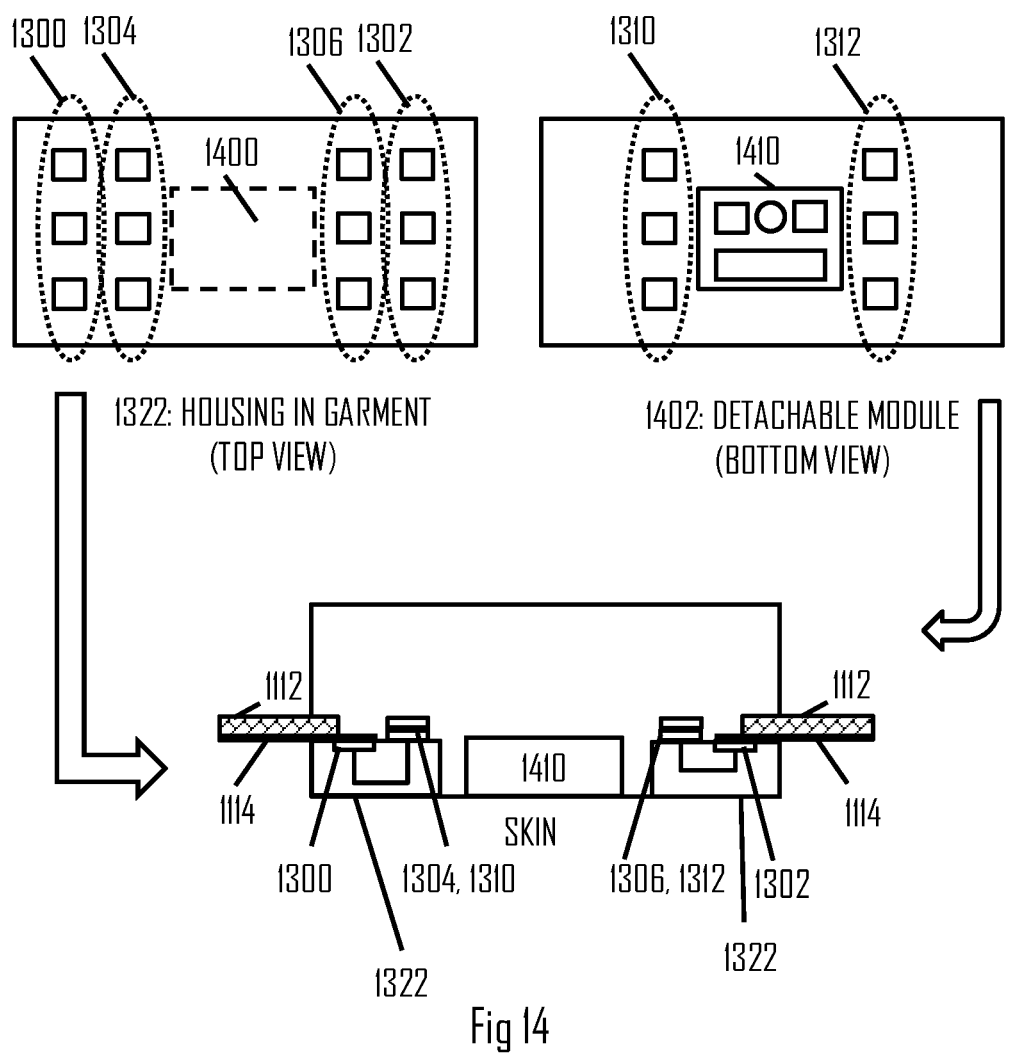

In an embodiment, the housing comprises a hole at the location where the casing is to be attached. FIG. 14 illustrates such an embodiment. The hole 1400 is illustrated in the housing, and, in the corresponding location in the casing 1402, a sensor head 1410 is disposed. A sensor may be provided on a surface of the casing in the sensor head 1410 designed to enter the hole 1400 and contact the skin. The sensor head 1410 may comprise a photo sensor, a photplethysmogram (PPG) sensor, ECG sensor and/or a temperature sensor. In such embodiment, the sensor head 1410 in the casing may replace one or more of the above-described electrodes, depending on the location of the casing 1402 in the garment. For example, if the location is above the heart level, the sensor head may replace one or more of the sensors 120, 124 and 134. If the location is below the heart level, the sensor head may replace one or more of the sensors 122, 126, 136. The sensor head may replace the ECG sensors 130, 132. The switching mechanism 520 may nevertheless work in the above-described manner.

Figure 15:
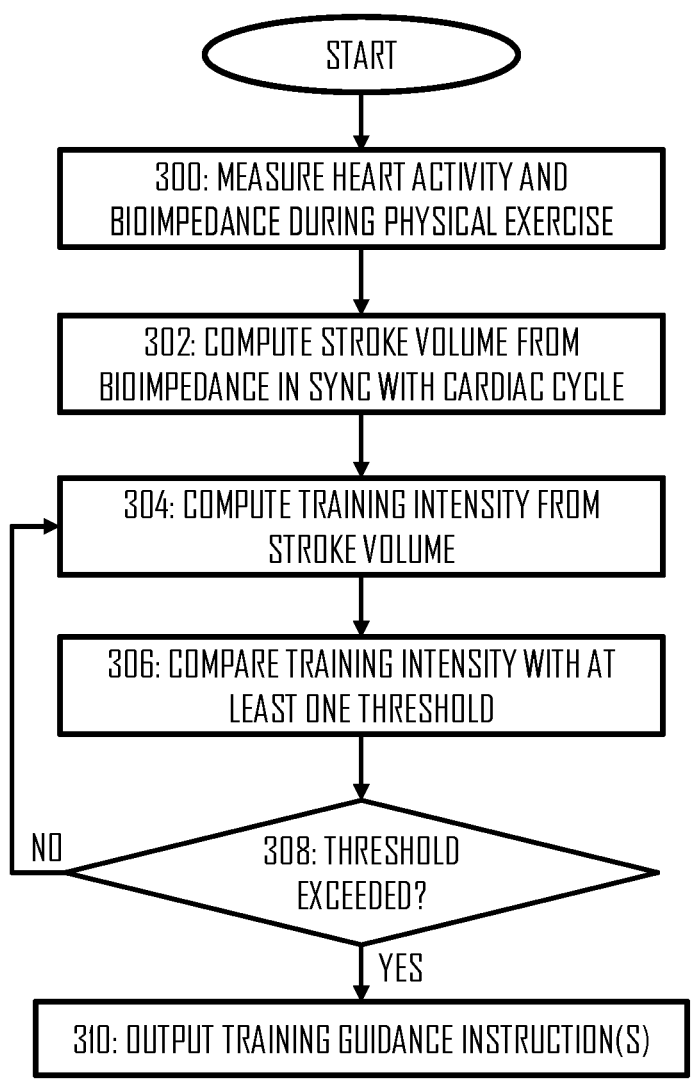
FIG. 15 illustrates a process for providing training guidance according to an embodiment of the invention.

Any one of the above-described measurement configurations may be used in the following embodiments for monitoring a physical exercise performed by the user 100. FIG. 15 illustrates a process for providing training guidance in connection with the physical exercise. The process may be executed by a training computer. Referring to FIG. 15, the process comprising: measuring (block 300), by using a heart activity sensor, heart activity of a user during the physical exercise; measuring (block 300), by using a bioimpedance measurement sensor, bioimpedance of the user during the physical exercise; computing (block 302), by a processing circuitry, a stroke volume from the bioimpedance synchronized to a cardiac cycle of the user by using the measured heart activity; computing (block 304), by the processing circuitry, training intensity for the physical exercise or a part of the physical exercise by using at least the computed stroke volume; and comparing (block 306 and 308), by the processing circuitry, the training intensity with at least one threshold and outputting (block 310) at least one training guidance instruction on the basis of the comparison.

Computation of the training intensity by using the stroke volume provides several advantages over conventional techniques that determine the training intensity from the heart rate. The heart rate does not yield the whole picture of cardiac output and user's effort level. This may lead for example to inaccurate training load or energy expenditure estimation. A typical example where the heart rate is a sub-optimal measure is high intensity interval training (HIIT) or strength training. After finishing a high-intensity work period, the heart rate drops relatively fast. This results in estimation of a mild training effect for the exercise although the user's muscles become exhausted. Stroke volume behaves differently and provides better correlation with tissue saturation index than the heart rate. The tissue saturation index is a measure of oxygenated haemoglobin in the blood and may be considered to represent true training intensity. The stroke volume may also increase after the heart rate has reached its maximum. It means that the estimation of the training intensity by using the stroke volume enables quantification of the training intensity when the heart rate has saturated. Accordingly, computation of the training intensity by using the stroke volume provides better accuracy in the estimation of the training intensity during and/or after the exercise.

In an embodiment, the training intensity is computed from the stroke volume.

In an embodiment, the processing circuitry computes heart rate from the measured heart activity, and computes the training intensity from cardiac output (CO) defined by a product of the computed stroke volume (SV) and the heart rate (HR) as:

$$CO(n)=SV(n)\times HR(n)$$

where n represents a time/sample index. As described above, the bioimpedance and the heart activity may be computed synchronously. The CO may thus be computed from samples or sample sets having the same time index or indices.

In an embodiment, the processing circuitry computes the heart rate from the measured heart activity, and further computes the training intensity from oxygen intake (VO2) defined by a product of the computed stroke volume, the heart rate, and a constant factor as:

$$VO2(n)=SV(n)\times HR(n)\times \text{avdiff}$$

where avdiff represents arteriovenous oxygen difference. avdiff is an indication of how much oxygen is removed from the blood in capillaries as the blood circulates in the body. In another words, it can be defined as a net difference of oxygen content between aorta and vein in terms of litres of oxygen per litre of blood. For the processing circuitry, this factor may be considered as a constant. It may be a predefiend user-specific parameter.

In an embodiment, the processing circuitry computes the heart rate from the measured heart activity, and further computes the training intensity from energy expenditure (EE) defined by a product of the computed stroke volume, the heart rate, the factor avdiff, and a predetermined user-related parameter as:

$$EE(n)=SV(n)\times HR(n)\times \text{avdiff}\times \text{oec}$$

where oec is an oxygen-to-energy coefficient that represents the user's ability to convert oxygen into energy, e.g. 5 kilocalories per litre of oxygen. EE may be a momentary energy expenditure at timing n.

Any one or a combination of the above-described training intensity measures may be used in block 304. All of them are training intensity metrics based on the stroke volume.

In an embodiment, the processing circuitry may utilize training intensity zones that are mapped to different training intensity ranges by using the stroke volume as a factor for the training intensity. In this embodiment, the processing circuitry may determine a plurality of training intensity zones on the basis of the stroke volume, wherein ranges of each training intensity zone is mapped to a unique range of stroke volume values. Thereafter, the processing circuitry may perform said comparison in blocks 306 and 308 by comparing the training intensity with at least one training intensity zone. In this embodiment, the at least one threshold may comprise at least one limit of the at least one training intensity zone.

The training intensity zones may be created for any one of the above-described training intensity measures, e.g. the SV, CO, VO2 or EE. All of them are based on the stroke volume and, thus represent the training intensity and training effect better than heart rate zones, for example. Another feature that distinguishes the stroke-volume-based training intensity zones from the heart rate zones, for example, is that the processing circuitry may indicate the zones to the user by using a different factor than that on which the zones are based, e.g. the stroke volume. The zone ranges may be mapped to the values of SV, CO, VO2, or EE but the training intensity zones may be indicated to the user by using verbal definitions or by percentages from the maximum value, as illustrated in the middle column of FIG. 4. Stroke volume or cardiac output values as such may not be illustrative to an average user and, therefore, use of more illustrative zone definitions serves the purpose of improved training guidance.

The heart rate may be a sub-optimal metric for measuring the training intensity and training load of a strength training or HIIT exercise. In a typical HIIT exercise which is an example of interval training, the user performs with high training intensity during work periods and rests or performs with mild training intensity during the rest periods. A general tendency with the TSI is that the TSI drops dramatically shortly after the start of the high-intensity work period and slowly recovers during the rest period. This indicates that the user works out in an anaerobic zone during the work period, which is typical for the HIIT exercise. The heart rate increases during the work period but falls quite quickly during the rest period, depending on the user's heart rate recovery capability. However, the stroke volume rises during the work periods and remains high during the work period. Eventually, the SV starts to drop but at a much slower pace than the heart rate, for example.

HIIT is an efficient exercise to maximize time at maximal SV. The SV has been shown to remain high during rest periods or even surpass SV values measured during the work periods, while VO2 as well as HR decrease quite rapidly during the rest periods. Reducing the training intensity of the rest periods or even resting during the rest periods of the HIIT exercise may therefore prolong the time to exhaustion. It may also allow the accumulation of more time on high-intensity zones, prolong accumulated time spent at maximal SV, maximal CO, maximal VO2, and/or maximal EE and lead to improved training benefit.

In an embodiment, the processing circuitry determines the training guidance such that the SV values are maximized. The processing circuitry may instruct the user to perform to maintain the SV above a determined threshold level. In an embodiment, upon detecting that the SV drops below a determined level, the processing circuitry may instruct the user to increase the training intensity. Figure illustrates an embodiment where the processing circuitry adapts the work periods of the interval exercise to the observations of the measured stroke volume. In this embodiment, the at least one threshold comprises a threshold for triggering the next work interval after a rest period of the physical exercise.

Figure 16:
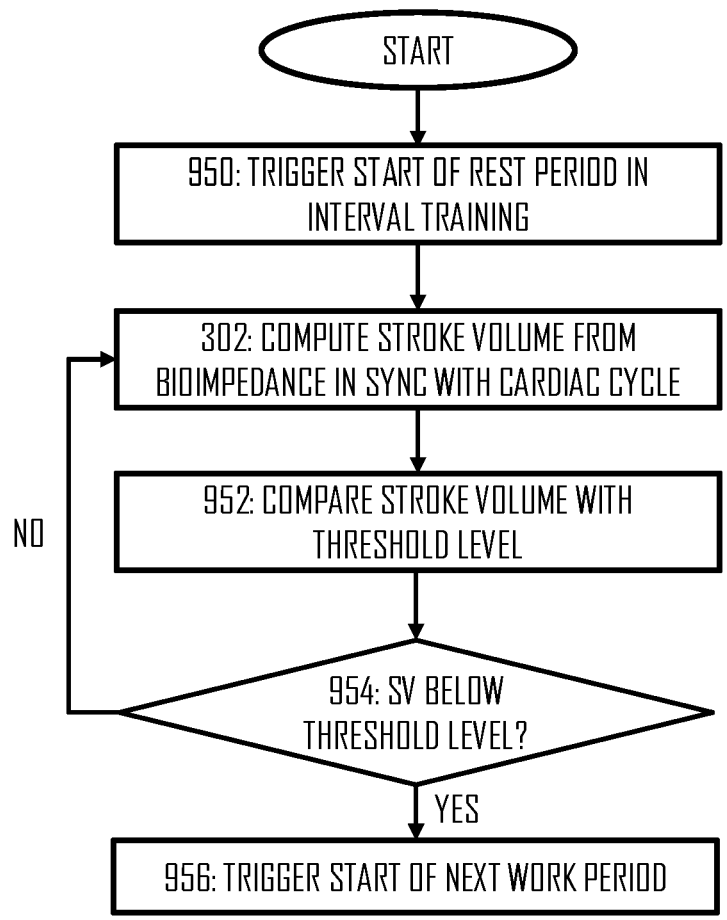
FIG. 16 illustrates a process for adapting duration of a rest period of an interval exercise according to an embodiment of the invention.

Referring to FIG. 16, the processing circuitry may trigger the start of the rest period in block 950. The trigger may be the end of the previous work period, and the end may be detected on the basis of measured time of the work period or measured training intensity accumulation during the work period. During the rest period, the processing circuitry may execute block 302 and compute the SV. In block 952, the processing circuitry compares the computed stroke volume with the threshold for triggering the next work interval. Upon detecting in block 954 that the comparison indicates that the stroke volume has dropped below a determined level defined by the threshold (YES in block 954), the processing circuitry outputs the training guidance instruction that instructs the user to start the next work interval (block 956). Otherwise, the process may return to block 302 to compute the next SV value. This embodiment enables maintenance of the SV above the threshold level, thus optimizing the training effect of the interval training.

In an embodiment, the determined level defined by the threshold is a selected drop of the stroke volume from a reference stroke volume measured at the start of the recovery interval, e.g. a value between 5 and 15 percent. In other words, when the SV has dropped for an amount determined by the value from the start of the rest period, the processing circuitry may trigger the next work period in block 956.

Figure 17:
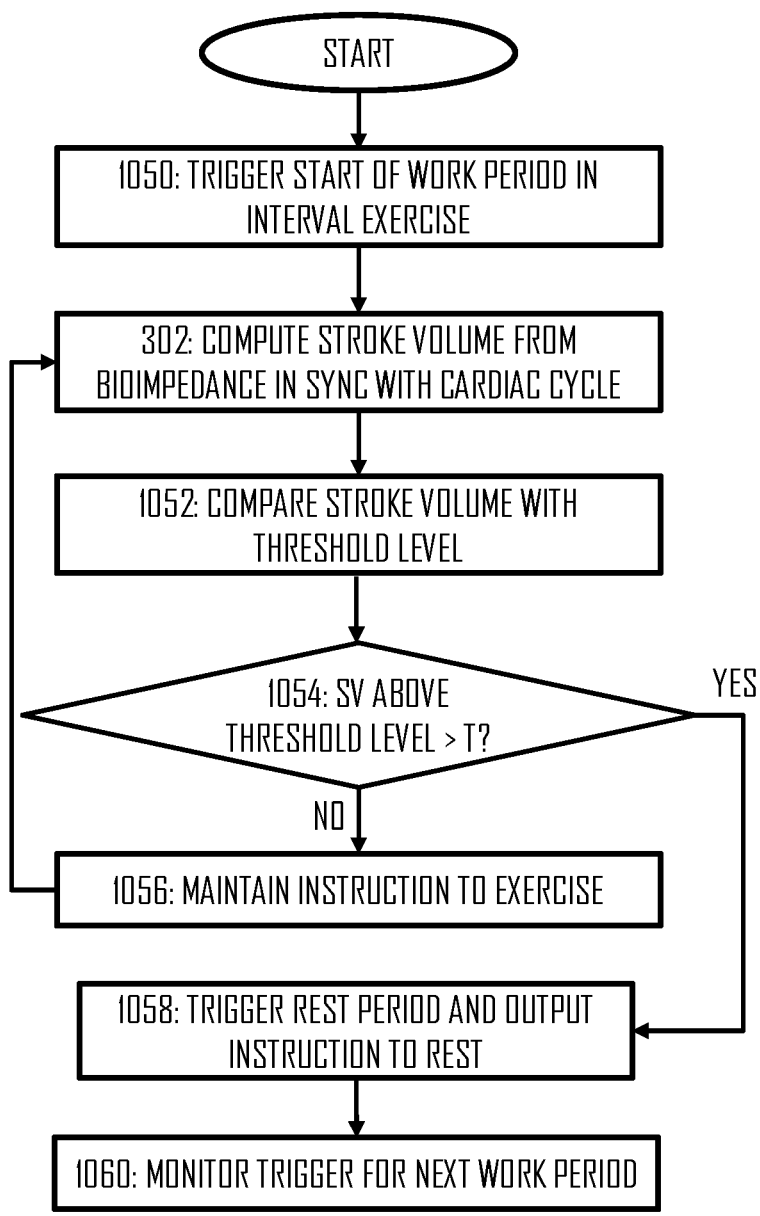
FIG. 17 illustrates a process for adapting duration of a work period of an interval exercise according to an embodiment of the invention.

In an embodiment, a similar approach for adapting the length of the work period is utilized by the processing circuitry and, in particular, the end of the work period. In this embodiment, the at least one threshold comprises a threshold indicating a minimum training intensity for a work period of the interval exercise. The processing circuitry accumulates time the stroke volume remains above the threshold during the work period, and outputs the training guidance instruction as an instruction to end the work period. The instruction is triggered by the processing circuitry upon detecting that the stroke volume has remained above the threshold for a determined target time interval T. FIG. 17 illustrates a process according to this embodiment.

Referring to FIG. 17, the processing circuitry triggers the start of the work period in the interval exercise in block 1050. The start may be triggered according to the process of FIG. 16 or by using a preset timing for the duration and end of the previous rest period (block 1050). During the work period, the processing circuitry may compute the stroke volume in the above-described manner in block 302. The computed stroke volume may be compared with the threshold indicating the minimum training intensity for the work period in block 1052. If the stroke volume indicates training intensity above the threshold level, the processing circuitry may accumulate the time the training intensity is above the threshold level (not shown). In block 1054, the processing circuitry compares the accumulated time with the target time interval T. If it is determined in block 1054 that the training intensity indicated by the stroke volume has remained above the threshold level for the target time interval or above the target time interval, the process may proceed to block 1058 where the processing circuitry triggers the end of the work period, start of the subsequent rest period, and outputs an instruction for the user to end the work period. Thereafter, the processing circuitry may start monitoring for the trigger of starting the next work period in block 1060, e.g. according to the embodiment of FIG. 9. Upon determining in block 1054 that the training intensity has not yet been above the threshold level long enough, the process may determine to maintain the instruction to continue the work period (block 1056) and then return to block 302.

Figure 18:
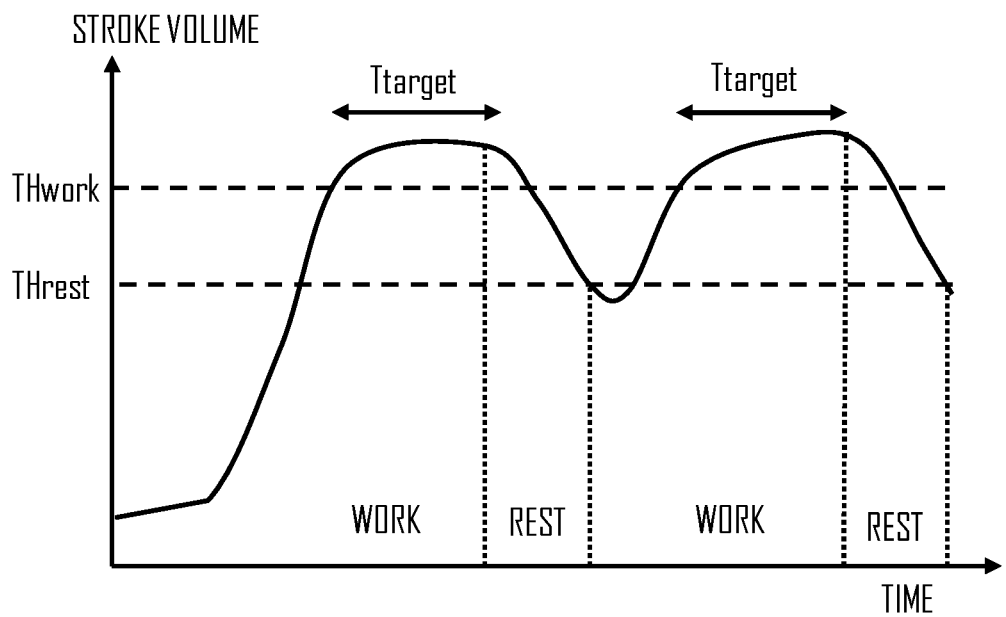
FIG. 18 illustrates an example of guidance during a physical exercise when employing the processes of FIGS. 16 and 17.

FIG. 18 illustrates an example of guidance during the exercise in the form of a curve illustrating a stroke-volume-based training intensity during the exercise. Y-axis of the graph of FIG. 18 represents the stroke-volume-based training intensity such as the SV, CO, VO2, or EE. Two thresholds are mapped to the Y-axis, $TH_{work}$ for the accumulation of the training intensity during the work period according to the embodiment of FIG. 17 and $TH_{rest}$ for triggering the end of the rest period according to the embodiment of FIG. 16. Referring to FIG. 18, the start of the interval exercise may be triggered in an arbitrary manner, e.g. the user starting the exercise and providing a start input to the training computer executing processes of FIGS. 16 and 17. Accordingly, the first work period starts. A warm-up phase may precede the first work period but that is omitted in this description for the sake of conciseness. During the first work period, the processing circuitry executes the process of FIG. 17, computes the stroke volume and compares the SV-based training intensity with the threshold $TH_{work}$. Whenever the training intensity is above the threshold, a time value is accumulated. When the time value reaches the target time interval $T_{target}$, the processing circuitry triggers the start of the rest period and starts comparing the stroke volume with the threshold $TH_{rest}$. When the stroke volume drops below the threshold $TH_{rest}$, the processing circuitry may trigger the start of the next work period. In this manner, the procedure may continue until the end of the interval exercise.

In an embodiment, the SV-based training intensity monitored in the embodiment of FIG. 16 may be different from the SV-based training intensity monitored in the embodiment of FIG. 17. For example, any one of the SV-based training intensities (SV, CO, VO2, EE) may be suitable for embodiment of FIG. 17 but it may be advantageous to measure only the SV in the embodiment of FIG. 16. Let us remind that the HR may be sub-optimal for the adaptation of the rest period because of the characteristic of dropping quickly. Accordingly, metrics involving the HR may also be less optimal than a metric not having the HR but having the SV.

Figure 19:
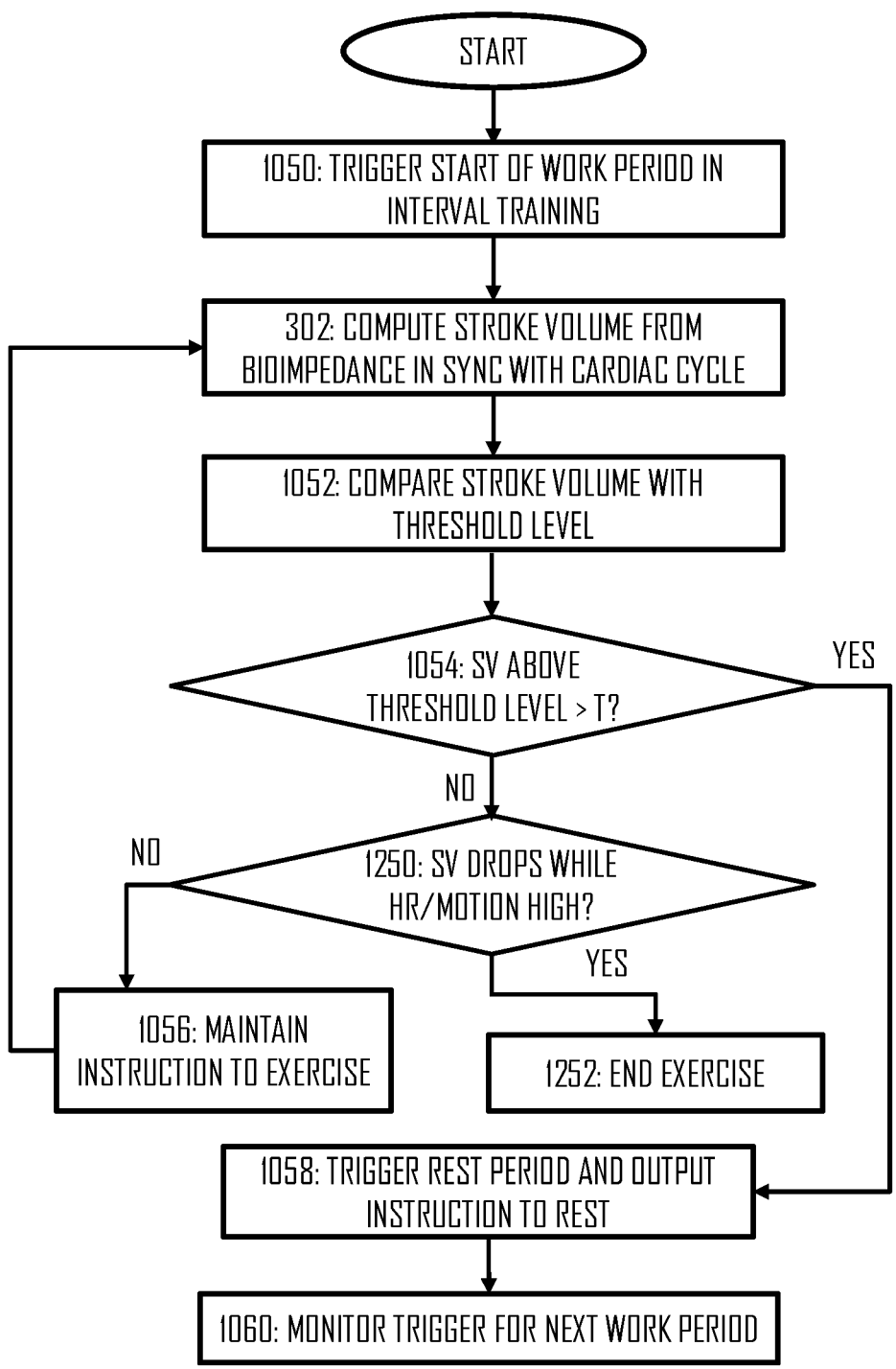
FIG. 19 illustrates a process for monitoring users fatigue level during the exercise according to an embodiment of the invention.

In an embodiment, the processing circuitry is configured to detect fatigue of the user from the computed stroke volume during the work interval and to output a training guidance instruction for the user to end the interval exercise. FIG. 19 illustrates an embodiment for cancelling the exercise upon detecting that the user is fatigued. The fatigue can be detected by evaluating the SV and the heart rate during the work period. Referring to FIG. 19, the processing circuitry may execute blocks 1050, 302, 1052, 1054, 1056, 1058, and 1060 in the above-described manner. Upon determining in block 1054 that the work period continues, the processing circuitry may next check the user's fatigue level. The checking may comprise evaluating the development of the SV. If the processing circuitry detects that the SV has dropped for at least a determined amount during the work period, e.g. by using threshold comparison, the processing circuitry may consider this as an indicator of fatigue and, next, check the development of the user's performance (block 1250). If one or more other indicators indicate that the user' is still performing with high intensity, the processing circuitry may in block 1250 determine that the user is fatigued and proceed to block 1252 where the processing circuitry ends the exercise. Block 1252 may comprise outputting an indication to the user to end the exercise. Block 1252 may comprise outputting an indication to the user that the user is possibly fatigued and should rest.

The one or more other indicators indicate that the user' is still performing with high intensity may comprise heart rate or motion intensity. The motion intensity may be measured by using a motion sensor, a force sensor, a cadence sensor, or a combination of these sensors. One or more thresholds may be employed in block 1250, e.g. one for determining the sufficient drop in the SV and another for determining that the training intensity remains sufficiently high for triggering the end of the exercise.

In an embodiment, the fatigue check of block 1250 may be carried out at another instance of the process or in a process parallel with respect to the process of FIG. 10 and/or FIG. 9.

Figure 20:
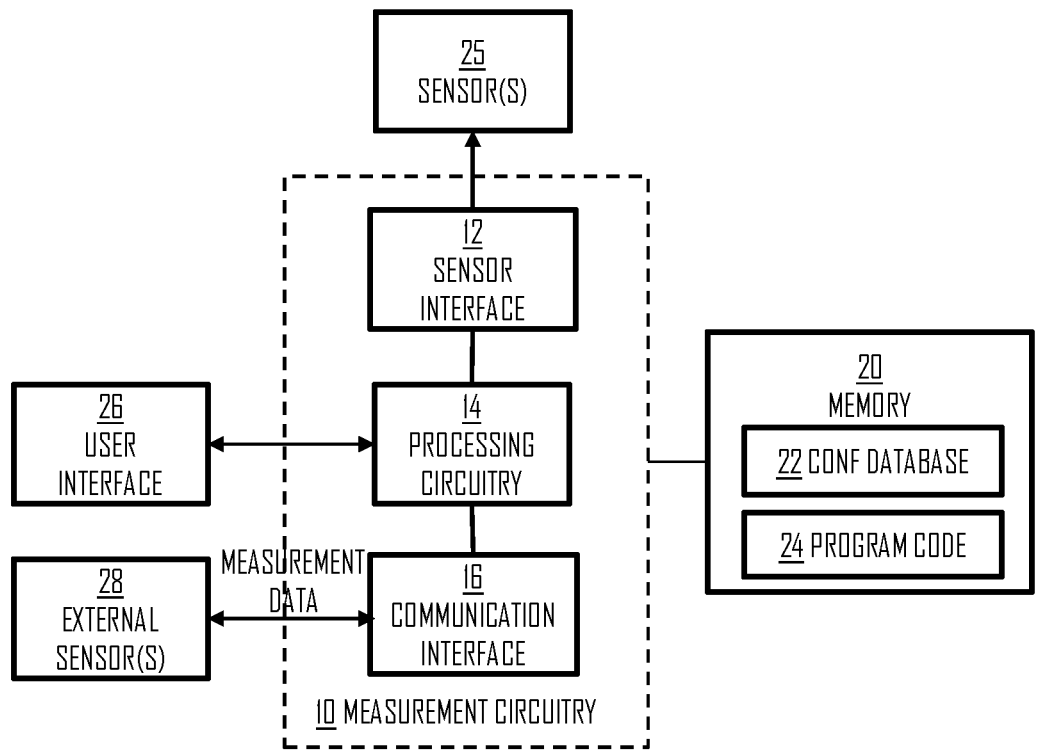
FIG. 20 illustrates a block diagram of an apparatus according to an embodiment of the invention.

FIG. 20 illustrates an embodiment of the training computer comprising the processing circuitry for carrying out the process of FIG. 15 or any one of its embodiments in a computer-implemented process. The training computer may be a smart phone, a tablet computer, a wrist computer, or even a server computer. The training computer may comprise a measurement circuitry 10 configured to perform computation and interfacing when monitoring the physical exercise performed by the user, e.g. during or after the exercise. The measurement circuitry 10 comprises the above-described processing circuitry 14. The measurement circuitry may further comprise a sensor interface 12 configured to provide a communication connection with one or more sensors 25 internal to the training computer. For example, a wrist computer may comprise an ECG sensor or a PPG sensor for measuring the heart activity. In some embodiments, the sensor interface and the internal sensors are omitted. The measurement circuitry may further comprise a communication interface 16 providing wireless communication connection with the external sensors 28, e.g. with the measurement circuitry 114 comprised in the garment. The communication interface 16 may support Bluetooth® protocol, for example Bluetooth Low Energy or Bluetooth Smart.

The training computer may further comprise a user interface 26 comprising a display screen and input means such as buttons or a touch-sensitive display. The processing circuitry 14 may output the instructions regarding the exercise to the user interface 26.

The training computer may further comprise or have access to at least one memory 20. The memory 20 may store a computer program code 24 comprising instructions readable and executable by the processing circuitry 14 and configuring the above-described operation of the processing circuitry 14. The memory 20 may further store a configuration database 22 defining parameters for the processing circuitry, e.g. the thresholds and/or the mapping table of the embodiment of FIG. 16.

Some embodiments as described herein may be carried out in the form of a computer process defined by a computer program or portions thereof. Embodiments of the methods described in connection with FIGS. 6, 7, 9, 15 to 17, and 19 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor.

The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a person of ordinary skill in the art.

Figure 21:
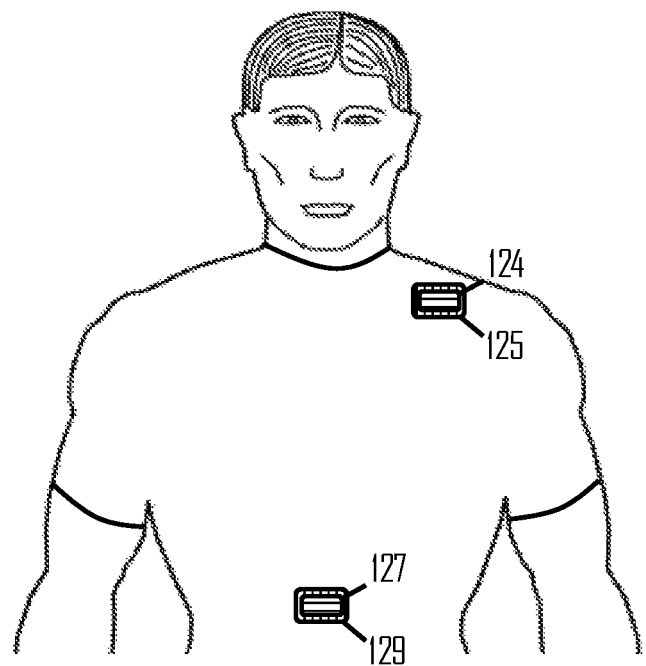
FIG. 21 illustrates an embodiment reducing undesired electric coupling between measurement electrodes

FIG. 21 illustrates yet another embodiment for implementing the electrodes and, particularly, improving electric coupling between the skin and the electrodes. The electrodes are illustrated in FIG. 21 by reference numbers 124 and 127. When the garment comprising the multiple electrodes gets wet during the exercise, for example, electric coupling between the electrodes through the garment may be formed. Such a coupling may degrade the performance of the measurements. In order to isolate this form of electric coupling, the electric path between the electrodes through the garment may be isolated. FIG. 21 illustrates an embodiment where the isolation is realized by isolating the electrodes from the garment by an isolation element 125, 129. The isolation element may be made of TPU, for example, or another electrically isolating material. The isolation element may be provided between the respective electrode and the garment, e.g. surrounding the respective electrode. In this manner, the electric coupling between the electrodes 124, 127 through the garment is isolated, thus improving the measurement accuracy.

Figure 22:
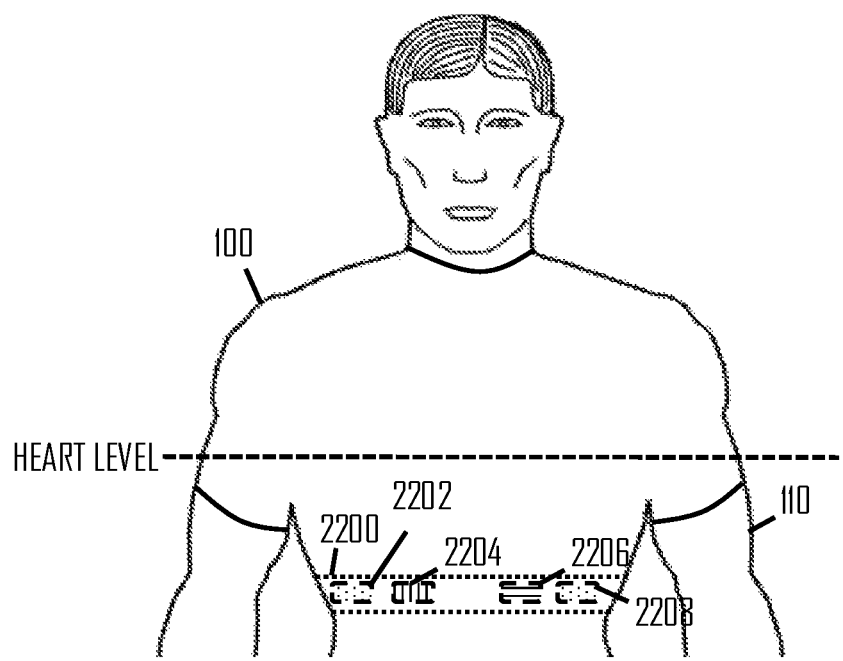
FIG. 22 illustrates an embodiment of the garment where the measurement electrodes are provided on the same side with respect to a heart level.
Figure 23:
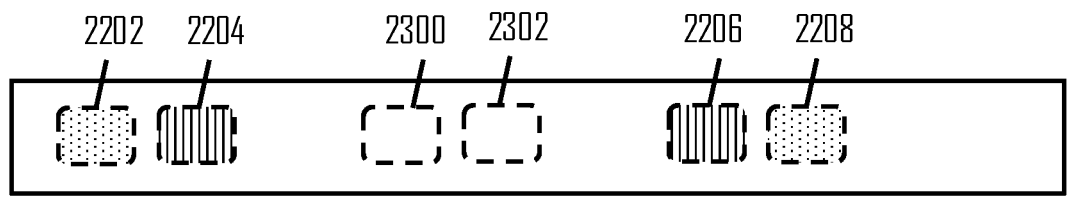
FIG. 23 illustrates an embodiment of the garment of FIG. 22.

FIGS. 22 and 23 illustrate embodiments where the garment is a strap 2200 to which the measurement electrodes have been integrated. The measurement electrodes may be arranged to the garment such that they reside on the same side of the heart level, e.g. above or below the heart level. In the embodiments of FIGS. 22 and 23, the measurement electrodes are disposed along a line, e.g. along a longitudinal axis of the strap. The measurement electrodes may comprise the above-described current feed electrodes 2202, 2208 and the voltage measurement electrodes 2204, 2206. The voltage measurement electrodes 2204, 2206 may be disposed between the current feed electrodes 2202, 2208 to improve the accuracy of the bioimpedance measurements. The gist may be that most of the current feed will flow along the direct route between the current feed electrodes. Therefore, the voltage measurement electrodes are on the path of the current flow, thus measuring the voltage on the part where most of the current flows. Furthermore, the voltage measurement electrode 2204 may be disposed directly next to the current feed electrode 2202 while the voltage measurement electrode 2206 may be disposed directly next to the current feed electrode 2208. The electrodes 2202, 2024 and the electrodes 2206, 2208 may each thus form a pair when observed spatial-wise. A separation between the electrodes 2202, 2204 and between the electrodes 2206, 2208 may be provided to prevent a short circuit. However, the closer the electrodes 2202, 2204 and electrodes 2206, 2208 are with respect to one another, the more accurate the bioimpedance measurement is.

In an embodiment, the voltage measurement electrodes may be used for computing the ECG, as described above.

One or more grounding electrodes 2300, 2302 may be integrated into the garment as well. The grounding electrodes may be disposed between the voltage measurement electrodes and between the current feed electrodes, as illustrated in FIG. 23. In other words, the voltage measurement electrode 2204 may be disposed between the grounding electrode 2300 and the current feed electrode 2202 while the voltage measurement electrode 2206 may be disposed between the grounding electrode 2302 and the current feed electrode 2208. In this embodiment, all the electrodes including the grounding electrodes are disposed on the front side of the garment, i.e. the side that contacts the user's chest. In another embodiment, at least the grounding electrodes 2300, 2302 are disposed on a back side of the garment, i.e. the side that contacts the user's back.

In an embodiment, at least one of the grounding electrodes couples to an electromagnetic interference (EMI) shield protecting the measurement electrodes against the EMI. While the electrodes 2202, 2204 and the electrodes 2206, 2208 may be disposed very close to one another, the grounding electrodes 2300, 2302 may be more separated from the measurement electrodes 2202 to 2208 to prevent grounding.

Figure 24:
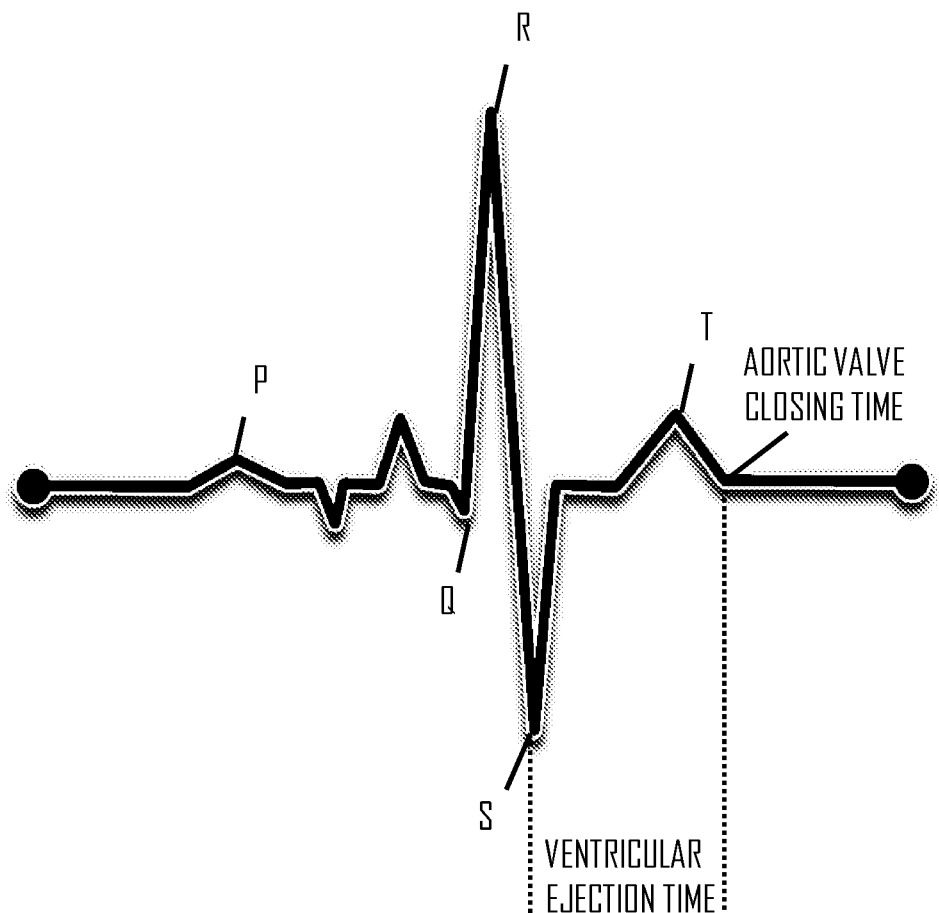
FIG. 24 illustrates an electrocardiogram waveform and different waves of the waveform.
Figure 25:
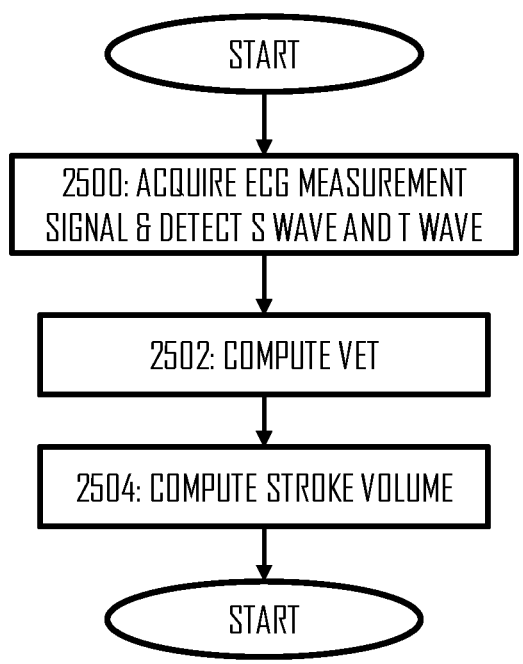
FIG. 25 illustrates an embodiment of a process for computing stroke volume on the basis of a ventricular ejection time of a measured electrocardiogram waveform.

FIGS. 24 and 25 illustrate another embodiment for computing the stroke volume by using the ECG measurement data acquired by using the measurement circuitry according to any one of the above-described embodiments or, in general, any ECG measurement circuitry. In the embodiment of FIGS. 24 and 25, the stroke volume computation is based on measuring a ventricular ejection time (VET) (block 2502) from the ECG measurement data acquired in block 2500. The VET may be computed by identifying (in block 2500) waveforms of the ECG signal that characterize the start and end of the VET. In particular, the start of the VET may be indicated by the S wave (see FIG. 24) while the end of the VET is indicated by an end of the T wave. The timing of the S wave and the end of the T wave may be detected by using various signal detection methods known in the art. For example, an integration method may be used, wherein the ECG measurement signal is integrated. The QRS complex shows in the integration signal as a high integration rise. End of that rise indicates the position of the S wave that may trigger the start of counting the VET. The subsequent T wave causes the integration signal to rise again and, after the rise ends, the T wave ends, triggering the end of counting the VET for that ECG wave. A number of consecutive ECG wave may be processed in the same manner to acquire multiple values for the VET. One or more of the VET values may then be input into the following Equation to compute the stroke volume SV (block 2504):

$$SV = Z_{amp} \times VET \times a$$

$Z_{amp}$ represents an amplitude of a measured bioimpedance signal according to any one of the above-described embodiments, e.g. an amplitude of a measured change of the bioimpedance. $Z_{amp}$ may be computed from the measured bioimpedance signal by computing a derivative of the measured bioimpedance signal thus acquiring a set of derivative samples, a differential signal. $Z_{amp}$ is thus an amplitude of the set of the differential signal. a represents volume of blood, and it may be considered to be a constant for the user which has been determined before-hand. The process of FIG. 25 may be executed by the processing circuitry 14 as a computer process.

In addition to the sensors and measurement circuits describe above, further sensors and measurement circuits may be integrated into the garment. Examples of such sensors include a temperature sensor, a humidity or moisture sensor configured to measure a sweat condition of the user, and an optical heart activity sensor configured to measure blood oximetry or photoplethysmogram (PPG) of the user. Measurement data of such additional sensors may be used in the computation of the above-described metrics such as the stroke volume or bioimpedance. The additional sensors may improve the accuracy of the computation.

It will be obvious to a person skilled in the art that, as the technology advances, the inventive concept can be implemented in various ways. The invention and its embodiments are not limited to the examples described above but may vary within the scope of the claims.

What is claimed is:

1. A system comprising:
a processor;
a chest strap made of flexible material;
a first measurement electrode integrated into the chest strap at a first location;
a second measurement electrode integrated into the chest strap at a second location different from the first location, wherein the first measurement electrode and the second measurement electrode are disposed in the chest strap along a longitudinal axis of the chest strap; and
a measurement circuitry configured to measure bioimpedance by arranging a current feed to the first measurement electrode and by measuring voltage from the second electrode and to transmit the measured bioimpedance, and to measure electrocardiogram by using at least one of the first measurement electrode and the second electrode or another electrode integrated into the chest strap, wherein the measuring is performed using multiple bioimpedance sample sets with samples having a same index in respective sample sets averaged to compute heart stroke volume; and
at least one motion sensor configured to measure motion of the chest strap at the first location and/or the second location, wherein the measurement circuitry is configured to perform motion compensation for the measured bioimpedance on the basis of the measured motion, and when the measured motion is above a pre-determined threshold or when a signal quality of the measured bioimpedance is below another pre-determined threshold, the processor is configured to compute the heart stroke volume on the basis of a mapping table that maps training intensities or heart rates to heart stroke volumes.

2. The system of claim 1, wherein the chest strap is an upper body chest strap, wherein the first measurement electrode is disposed above a heart level and the second measurement electrode is disposed below the heart level.

3. The system of claim 1, wherein the chest strap is an upper body chest strap, wherein both the first measurement electrode and the second measurement electrode is disposed below the heart level or above the heart level.

4. The system of claim 1, wherein the chest strap has a backside arranged to face a backside of a user wearing the chest strap and further has a front side arranged to face a front side of the user, wherein the first measurement electrode is disposed in the chest strap on at least the backside of the chest strap.

5. The system of claim 4, wherein the second electrode is disposed in a chest area of the chest strap, wherein the chest strap is arranged to be form-fitting at the location of the second electrode.

6. The system of claim 4, wherein the first measurement electrode is elongated and extends from the backside of the chest strap to the front side of the chest strap.

7. The system of claim 1, wherein the measurement circuitry is configured in a casing detachable from the chest strap, and wherein the chest strap further comprises a housing configured to receive and position the casing and to connect the measurement circuitry to the first and second measurement electrodes.

8. The system of claim 7, wherein the casing comprises a sensor head coupled to the measurement circuitry, wherein the housing comprises a hole to receive the sensor head, and wherein the sensor head is arranged to contact user's skin when the casing is connected to the housing and when the chest strap is worn by the user.

9. The system of claim 8, wherein the sensor head comprises at least one of a photoplethysmogram sensor head and a temperature sensor head.

10. The system of claim 1, the system further comprising a third electrode and a fourth electrode forming a current feed circuitry, wherein the first measurement electrode, the second measurement electrode, the third measurement electrode, and the fourth measurement electrode, are disposed in the chest strap along a line such that the first measurement electrode is directly next to the third measurement electrode and the second measurement electrode is directly next to the fourth measurement electrode.

11. The system of claim 10, further comprising at least one grounding electrode disposed between the first measurement electrode and the second measurement electrode.

12. The system of claim 1, wherein the measurement circuitry is configured to compute a ventricular ejection time from the measured electrocardiogram and to compute the heart stroke volume on the basis of at least the computed ventricular ejection time.

13. The system of claim 1, wherein the measurement circuitry is configured to compute a ventricular ejection time from the measured electrocardiogram and to compute the heart stroke volume on the basis of at least the mapping table when the measured motion is above the predetermined threshold.

14. A system comprising:
a processor; a chest strap made of flexible material
a first measurement electrode integrated into the chest strap at a first location;
a second measurement electrode integrated into the chest strap at a second location different from the first location, wherein the first measurement electrode and the second measurement electrode are disposed in the chest strap along a longitudinal axis of the chest strap; and
a measurement circuitry configured to measure bioimpedance by arranging a current feed to the first measurement electrode and by measuring voltage from the second electrode and to transmit the measured bioimpedance, and to measure electrocardiogram by using at least one of the first measurement electrode and the second electrode or another electrode integrated into the chest strap, wherein the measuring is performed using multiple bioimpedance sample sets with samples having a same index in respective sample sets averaged to compute heart stroke volume, wherein the measurement circuitry comprises at least one switch switching a function of at least one of the measurement electrodes between electrocardiogram measurement and bioimpedance measurement; and
at least one motion sensor configured to measure motion of the chest strap at the first location and/or the second location, wherein the measurement circuitry is configured to perform motion compensation for the measured bioimpedance on the basis of the measured motion, and when the measured motion is above a pre-determined threshold or when a signal quality of the measured bioimpedance is below another pre-determined threshold, the processor is configured to compute the heart stroke volume on the basis of a mapping table that maps training intensities or heart rates to heart stroke volumes.

15. The system of claim 14, wherein the at least one switch switches the function of the measurement electrodes between at least two of the following measurement modes: full electrocardiogram mode where all measurement electrodes are used to measure electrocardiogram, a full bioimpedance measurement mode where all measurement electrodes are used to measure bioimpedance, and a hybrid measurement mode where a first subset of the measurement electrodes are used to measure electrocardiogram and a second subset of the measurement electrodes are used to measure bioimpedance.

* * * * *